(12) United States Patent
Pfannenstiel et al.

(10) Patent No.: US 12,268,440 B2
(45) Date of Patent: Apr. 8, 2025

(54) MINIMALLY INVASIVE MICROWAVE ABLATION DEVICE

(71) Applicants: Kansas State University Research Foundation, Manhattan, KS (US); Precision Microwave Inc., Manhattan, KS (US)

(72) Inventors: Austin Pfannenstiel, Manhattan, KS (US); Hojjatollah Fallahi, Manhattan, KS (US); Punit Prakash, Manhattan, KS (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 401 days.

(21) Appl. No.: 17/465,169

(22) Filed: Sep. 2, 2021

(65) Prior Publication Data
US 2021/0393328 A1 Dec. 23, 2021

Related U.S. Application Data

(63) Continuation of application No. 16/881,780, filed on May 22, 2020, now Pat. No. 11,135,010.
(Continued)

(51) Int. Cl.
*A61B 18/18* (2006.01)
*A61B 18/00* (2006.01)

(52) U.S. Cl.
CPC ............. *A61B 18/1815* (2013.01); *A61B 2018/00077* (2013.01); *A61B 2018/00577* (2013.01);
(Continued)

(58) Field of Classification Search
CPC ............ A61B 18/1477; A61B 18/1815; A61B 2018/00023; A61B 2018/00029; A61B 2018/00077; A61B 2018/00107; A61B 2018/00166; A61B 2018/00202; A61B 2018/00482; A61B 2018/00529; A61B 2018/00541; A61B 2018/00577; A61B 2018/00595; A61B 2018/00601; A61B 2018/00642; A61B 2018/00773;
(Continued)

(56) References Cited

U.S. PATENT DOCUMENTS 5,057,106 A  10/1991  Kasevich et al.
5,061,267 A  10/1991  Zeiher
(Continued)

OTHER PUBLICATIONS

International Search Report and Written Opinion in corresponding PCT/US2020/034290, dated Aug. 17, 2020.
(Continued)

*Primary Examiner* — Michael F Peffley
(74) *Attorney, Agent, or Firm* — Hovey Williams LLP

(57) ABSTRACT

An electrosurgical device (10) is provided that is operable to deliver microwave energy within a controlled angular expanse to cause targeted tissue ablation. The device (10) comprises a blocking or reflecting material such as cylindrical members (34) that are laterally spaced from the antenna (20) that is operable to emit the microwave energy. The reflecting material creates regions in and/or surrounding the device into which sensors (51), such as thermocouple wires, may be placed to monitor a condition associated with the device or the patient's body.

16 Claims, 12 Drawing Sheets

Related U.S. Application Data

(60) Provisional application No. 62/852,671, filed on May 24, 2019.

(52) U.S. Cl.
CPC ............... *A61B 2018/00595* (2013.01); *A61B 2018/00601* (2013.01); *A61B 2018/00821* (2013.01); *A61B 2018/183* (2013.01); *A61B 2018/1861* (2013.01); *A61B 2218/002* (2013.01)

(58) Field of Classification Search
CPC ........... A61B 2018/00779; A61B 2018/00791; A61B 2018/00875; A61B 2018/00898; A61B 2018/00994; A61B 2018/1266; A61B 2018/183; A61B 2018/1853; A61B 2018/1861; A61B 2018/1869; A61B 2018/1884; A61B 2018/1892; A61B 2218/002
USPC ........................................................ 607/156
See application file for complete search history.

(56) References Cited

U.S. PATENT DOCUMENTS

| | | | |
|---|---|---|---|
| 5,314,466 A * | 5/1994 | Stern | A61B 18/1492 606/41 |
| 5,500,012 A | 3/1996 | Brucker et al. | |
| 5,672,174 A | 9/1997 | Gough et al. | |
| 6,245,062 B1 | 6/2001 | Berube et al. | |
| 6,471,696 B1 | 10/2002 | Berube et al. | |
| 6,634,055 B1 | 10/2003 | De Block | |
| 6,673,068 B1 | 1/2004 | Berube | |
| 6,878,147 B2 | 4/2005 | Prakash et al. | |
| 6,962,587 B2 * | 11/2005 | Johnson | A61B 18/1477 606/41 |
| 7,033,352 B1 * | 4/2006 | Gauthier | A61B 18/18 607/101 |
| 7,311,703 B2 | 12/2007 | Turovskiy et al. | |
| 7,410,485 B1 | 8/2008 | Fink et al. | |
| 8,235,981 B2 | 8/2012 | Prakash et al. | |
| 8,292,881 B2 | 10/2012 | Brannan et al. | |
| 8,328,801 B2 * | 12/2012 | Brannan | A61B 18/14 606/41 |
| 8,965,536 B2 | 2/2015 | Bonn et al. | |
| 9,119,650 B2 | 9/2015 | Brannan et al. | |
| 2003/0109862 A1 | 6/2003 | Prakash et al. | |
| 2003/0195499 A1 | 10/2003 | Prakash et al. | |
| 2006/0138122 A1 | 6/2006 | Gauthier et al. | |
| 2012/0303022 A1 | 11/2012 | Deshpande | |
| 2017/0100186 A1 | 4/2017 | Brannan et al. | |
| 2017/0252106 A1 | 9/2017 | Brannan | |
| 2017/0265940 A1 * | 9/2017 | Prakash | A61B 17/00234 |
| 2018/0261922 A1 | 9/2018 | Behdad et al. | |

OTHER PUBLICATIONS

Office Action in corresponding U.S. Appl. No. 16/881,780, dated Feb. 24, 2021.

European Search Report in corresponding EP20814643.1-1126, dated May 11, 2023.

* cited by examiner

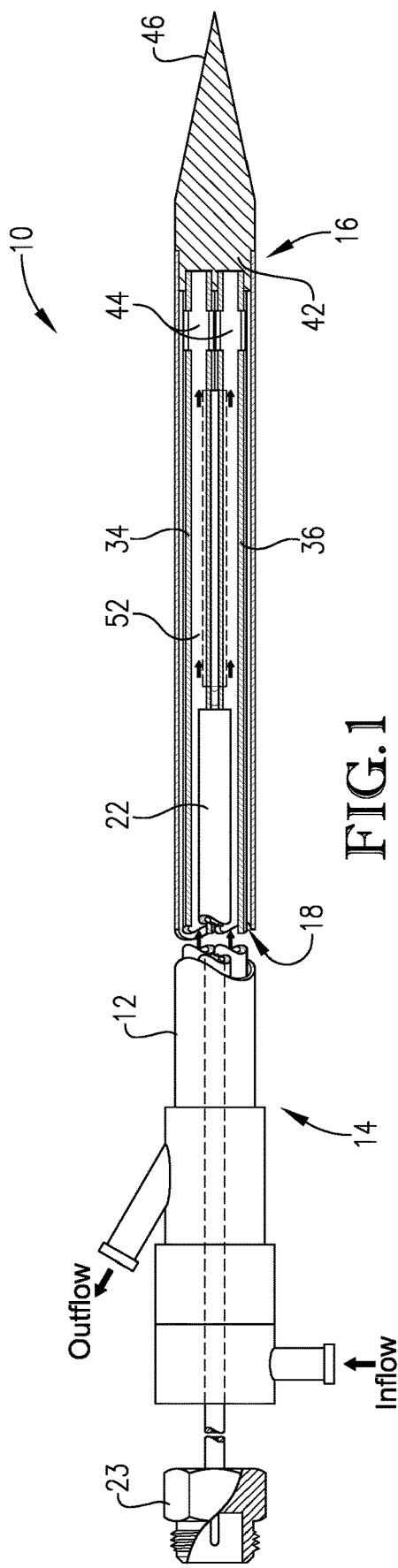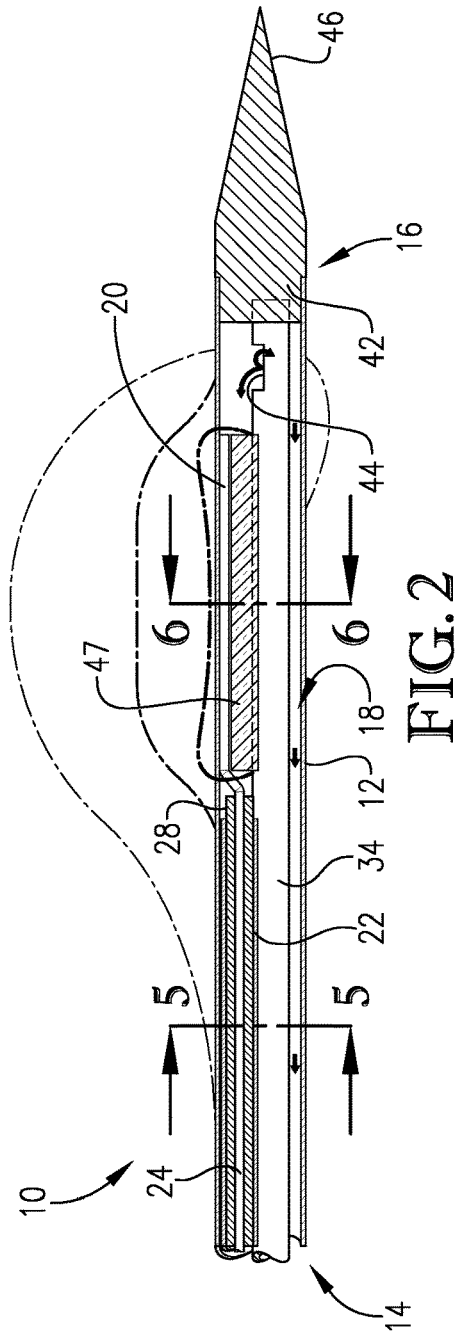

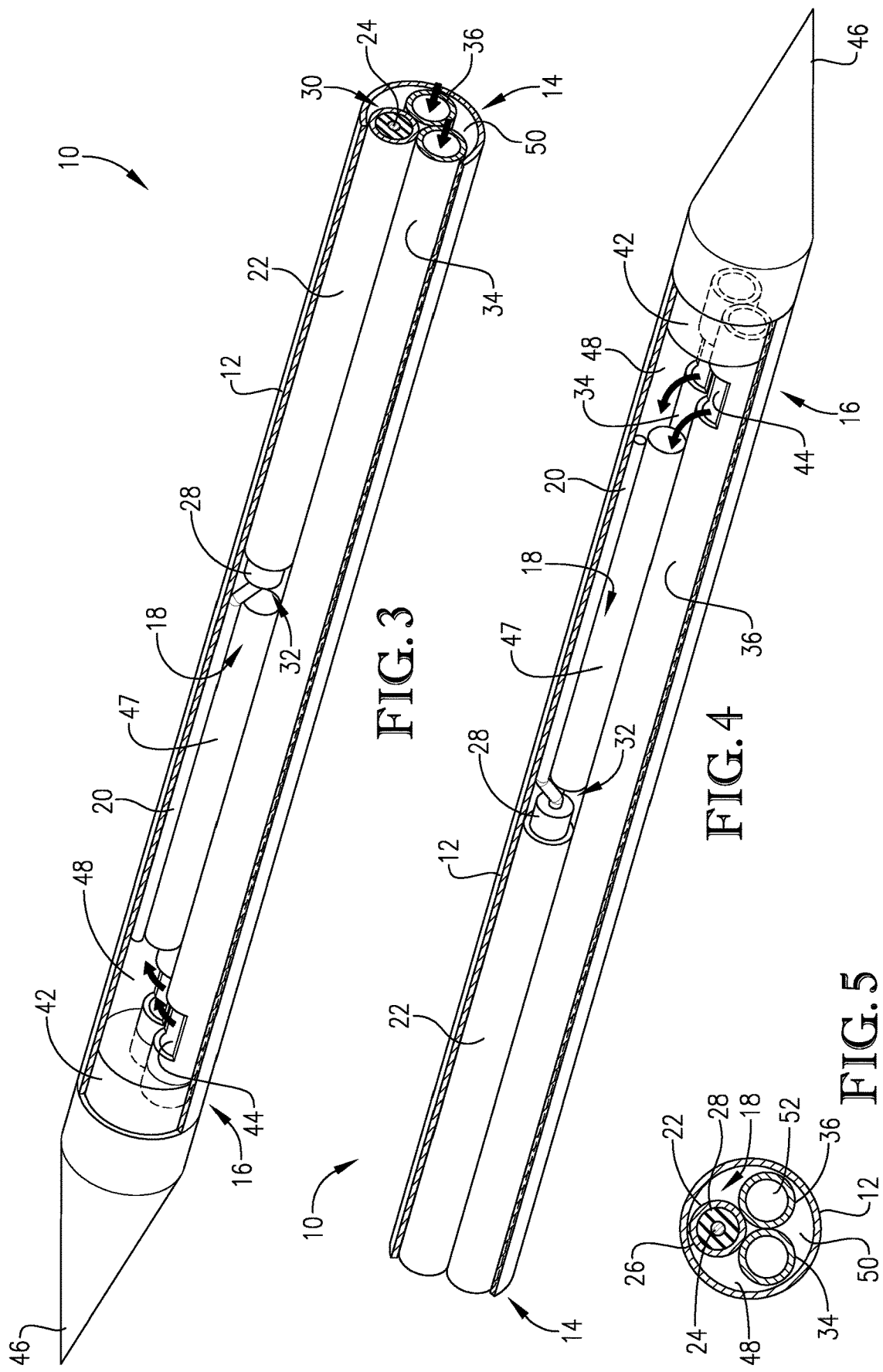

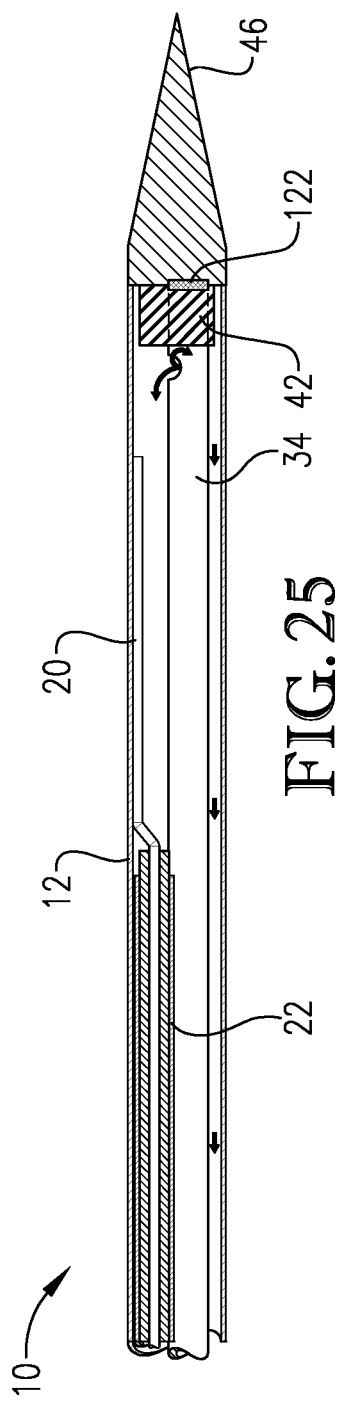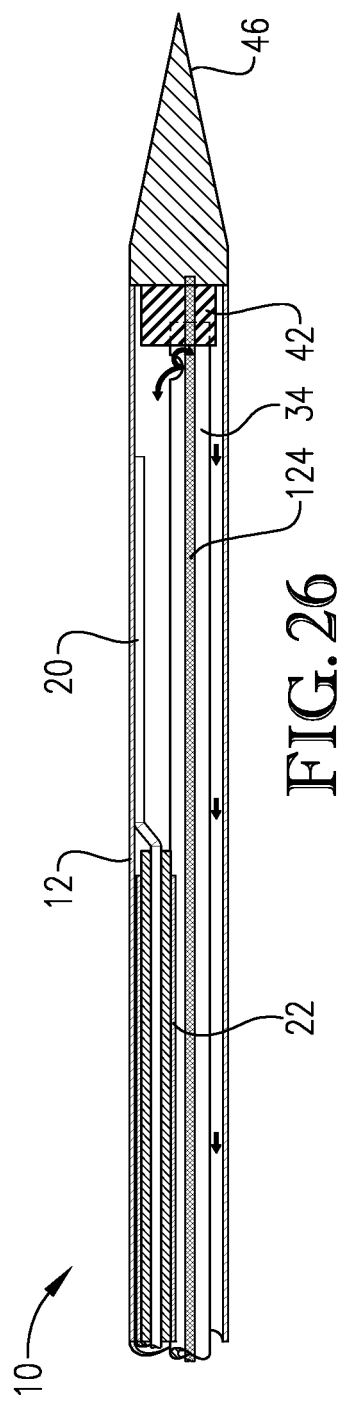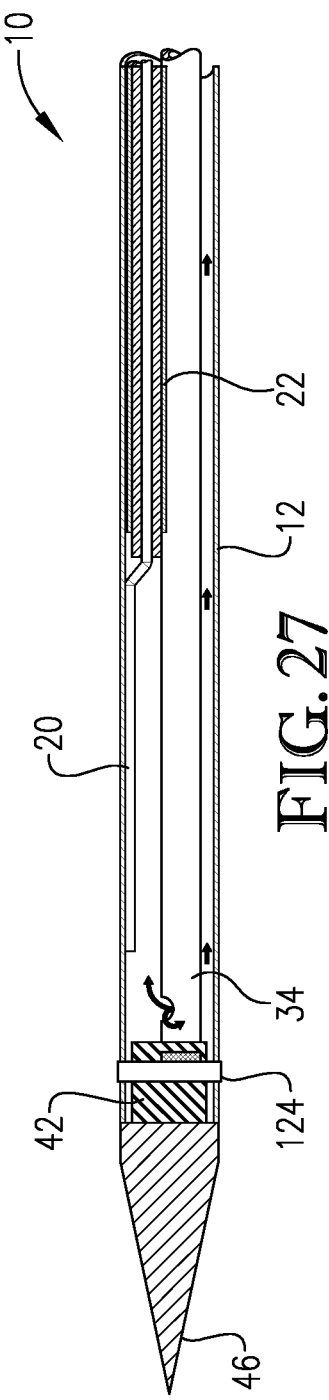

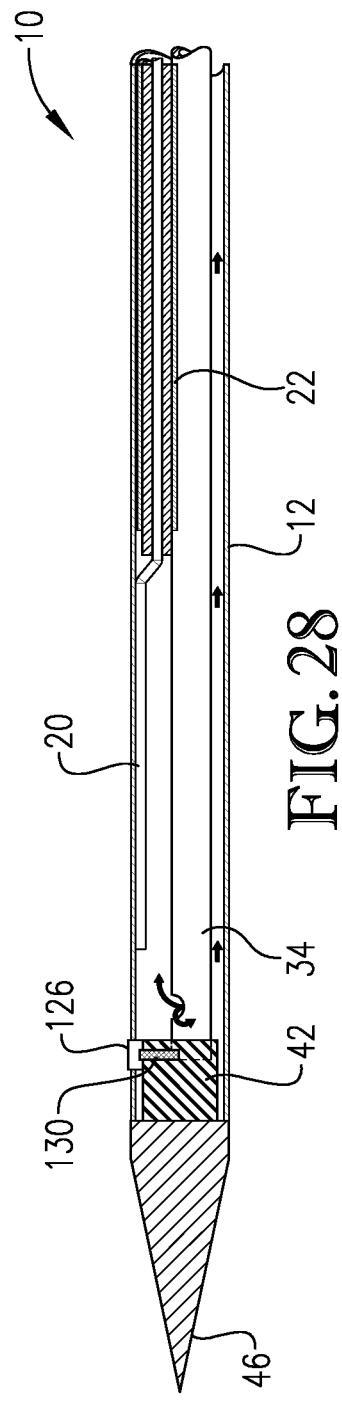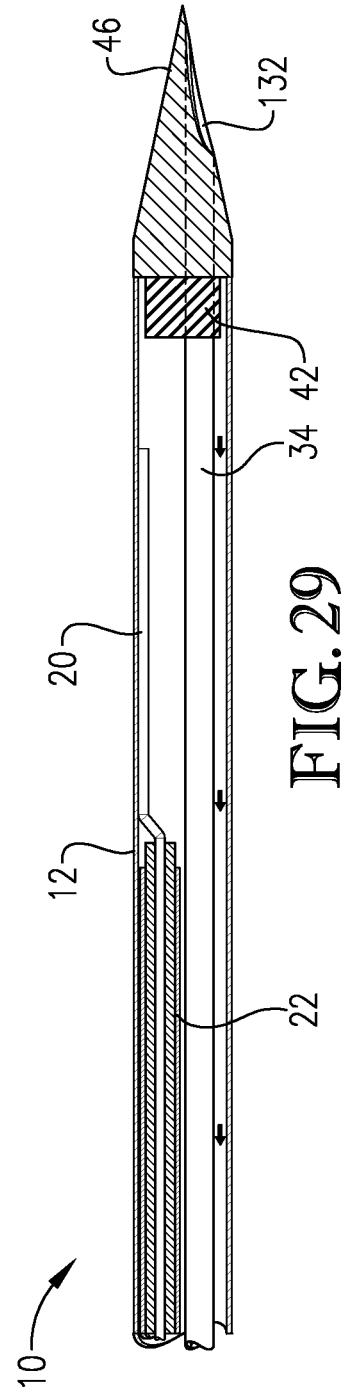

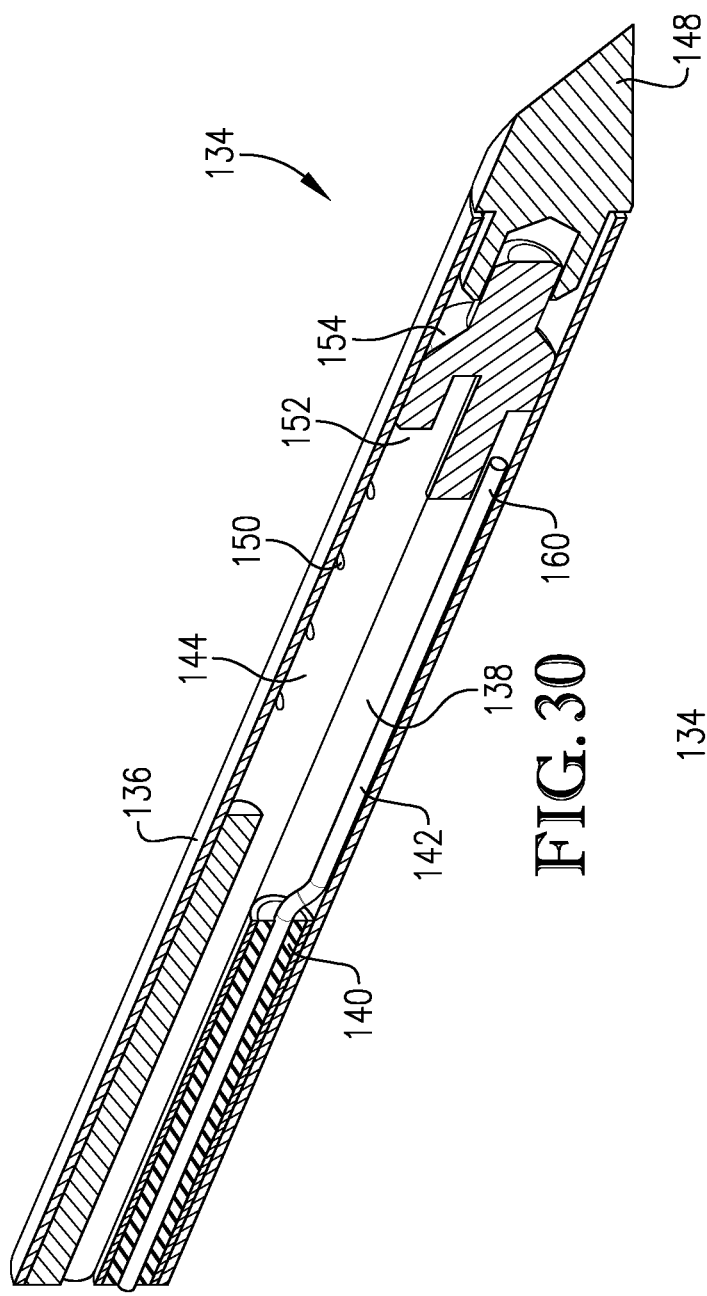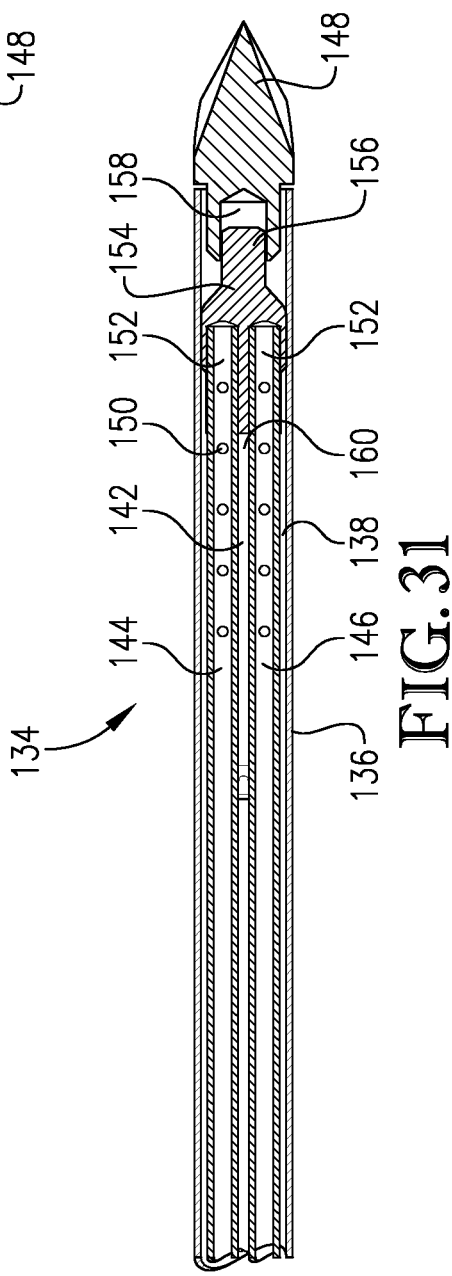

MINIMALLY INVASIVE MICROWAVE ABLATION DEVICE

RELATED APPLICATION

This application is a continuation of U.S. patent application Ser. No. 16/881,780, filed May 22, 2020, which issued as U.S. Pat. No. 11,135,010 and claims the benefit of U.S. Provisional Patent Application No. 62/852,671, filed May 24, 2019, each of which is incorporated by reference herein in its entirety.

STATEMENT REGARDING FEDERALLY SPONSORED RESEARCH OR DEVELOPMENT

This invention was made with government support under grant number 1819177 awarded by the National Science Foundation (NSF). The government has certain rights in the invention.

BACKGROUND OF THE INVENTION

Field of the Invention

The present invention is generally directed toward electrosurgical devices operable to deliver microwave energy of sufficient intensity to cause targeted ablation of tissue located within a human or animal body. The electrosurgical device is capable of delivering the microwave energy within a controlled angular expanse using blocking and/or reflecting material located within the device.

Description of the Prior Art

Microwave ablation (MWA) is an increasingly used thermal therapy modality for minimally-invasive treatment of tumors and benign disease. Other energy sources for thermal ablation include radiofrequency current, lasers, catheter-based ultrasound applicators, and cryoablation. These procedures may be performed minimally invasively (typically under guidance of ultrasound, or computerized tomography guidance), laparoscopically, or under open surgery. MWA has found clinical applications in the treatment of tumors in the liver, kidney, lung, and bone, as well for treatment of cardiac arrhythmias, ablation of benign prostate tissue to treat hyperplasia (BPH), ablation of the uterine endometrial lining to treat menorrhagia, ablation of the esophageal wall for treating Barrett's esophagus and GERD, ablation of nerves for treating back pain, and ablation of renal nerves for treating chronic high blood pressure.

During an ablation procedure, an antenna is inserted into the target tissue or placed in close proximity thereto and radiates electromagnetic power at microwave frequencies; most currently available devices operate within frequency bands approved for industrial, scientific, and medical (ISM) use, centered at 915 MHz and 2.45 GHz. Electromagnetic power radiated from the antenna is deposited in the electromagnetic lossy tissue leading to heating via dielectric hysteresis. While thermal damage following ablation is a complex function of the time-temperature history during heating, temperatures in excess of 60° C. lead to near-instantaneous cell death by coagulative necrosis. Irreversible, but not lethal, thermal damage may occur in cells heated above 42° C. A fundamental principal of successful ablation is the creation of an ablation zone that sufficiently covers the entire target while providing a margin of safety for adjacent tissues.

In the past, microwave ablation devices were configured to be inserted into the center of the targeted tissue, and the ablation zone grows radially outward. When ablating targets in proximity to critical structures, caution needed to be taken to ensure complete thermal coverage of the target volume, while precluding thermal damage to non-targeted tissues. These devices were based on coaxial antenna designs and had generally axially symmetric radiation patterns. Generally, there was no control of the energy deposition pattern in the angular expanse. Spatial control of the energy deposition pattern was limited to control of heating along the antenna length, for example, as achieved by employing a sleeve/choke element and/or active cooling.

More recently, directional microwave applicators such as those described in U.S. Pat. Nos. 7,410,485 and 8,235,981 and U.S. Patent Application Publication No. 2017/0265940 offered the ability to control the energy deposition pattern along the angular expanse through the use of reflectors and/or window structures formed in the tubular outer wall of the applicator. Because these devices are configured for percutaneous use, device diameter and rigidity are important considerations. It is highly desirable for the device to have as small a diameter as possible to permit the least invasive insertion into the patient's body. In addition, because the tissues through which the device must be inserted can be thick and fibrous, the device must possess sufficient rigidity and internal strength to avoid being deflected along its path of insertion so that it can predictably reach the targeted tissue.

It has been discovered that it can be difficult to achieve sufficiently small device diameters while maintaining sufficient device rigidity in certain prior art designs. Therefore, a need exists in the art for an improved directional microwave applicator that achieves these objectives.

SUMMARY OF THE INVENTION

According to one embodiment of the present invention, there is provided a device for delivering electromagnetic energy to a target tissue within a human or animal body. The device comprises an elongate body comprising a proximal end, a distal end, and at least one lumen interconnecting the proximal and distal ends. An antenna is located within the at least one lumen and configured to emit electromagnetic energy therefrom sufficiently strong to cause tissue ablation. The device also comprises at least one elongate cylindrical member located within the same or a different lumen as the antenna. The at least one elongate cylindrical member is disposed laterally from the antenna. Preferably, the at least one elongate cylindrical member comprises a distal end segment that is secured to the elongate body distal end.

According to another embodiment of the present invention, there is provided a device for delivering electromagnetic energy to a target tissue within a human or animal body. The device comprises an elongate body comprising a proximal end, a distal end, and a lumen interconnecting the proximal and distal ends. An antenna is located within the lumen and configured to emit electromagnetic energy therefrom sufficiently strong to cause tissue ablation. The device further comprises a plurality of elongate cylindrical members, which are preferably electrically conductive, located within the lumen and disposed laterally from the antenna. The plurality of elongate cylindrical members is configured to reflect a portion of the electromagnetic energy emitted from the antenna and to shield posterior tissue from the electromagnetic energy.

According to yet another embodiment of the present invention, there is provided a device for delivering electromagnetic energy to a target tissue within a human or animal body comprising an elongate body formed from a synthetic resin material, an antenna, and at least one electrically conductive member. The elongate body comprises a proximal end, a distal end, and at least two lumens interconnecting the proximal and distal ends. The antenna is located within one of the at least two lumens and configured to emit electromagnetic power therefrom sufficiently strong to cause tissue ablation. The at least one reflective member is located within one other of the at least two lumens and is spaced apart and disposed laterally from the antenna.

According to still another embodiment of the present invention, there is provided a device for delivering electromagnetic energy to a target tissue within a human or animal body comprising an elongate body having a proximal end and a distal end, an antenna, at least one elongate cylindrical member, and a rigid spacer located at the distal end of the elongate body into which a distal portion of the antenna is received. The elongate body comprises at least one lumen interconnecting the proximal and distal ends. The antenna is located within the at least one lumen and configured to emit electromagnetic power therefrom sufficiently strong to cause tissue ablation. The at least one elongate cylindrical member located within the same or a different lumen as the antenna and is disposed laterally from the antenna.

According to still another embodiment of the present invention, there is provided a method for ablating tissue within a body. The method comprises inserting a device for delivering electromagnetic energy to a target tissue as described herein into the body containing the tissue to be ablated. The device antenna is positioned adjacent to the tissue to be ablated, the tissue to be ablated residing substantially to one side of the antenna. The device is activated thereby causing the antenna to emit electromagnetic radiation that is sufficiently strong to cause ablation of the tissue.

According to yet another embodiment of the present invention, there is provided a method of ablating tissue within an organ of a body in which a directional microwave ablation device is inserted into the body containing the tissue to be ablated. The device comprises an antenna that is configured to emit electromagnetic energy therefrom that is sufficiently strong to cause tissue ablation. The device is positioned in direct contact with, but without penetrating, the organ. The device is then activated thereby causing the antenna to emit electromagnetic radiation that is sufficiently strong to cause ablation of the tissue within the organ.

According to yet a further embodiment of the present invention, there is provided a method of ablating a tumor within a body in which a directional microwave ablation device is inserted into the tumor to be ablated. The device comprises an antenna that is configured to emit electromagnetic energy therefrom that is sufficiently strong to cause tissue ablation. The device is activated thereby causing the antenna to emit electromagnetic radiation that is sufficiently strong to cause ablation of a portion of the tumor. The device is then rotated within the tumor without removing the device from the tumor, and then another portion of the tumor is ablated with the device.

BRIEF DESCRIPTION OF THE DRAWINGS

FIG. 1 is a schematic, partially sectioned illustration of one embodiment of a directional ablation device according to the present invention;

FIG. 2 is a partial cross-sectioned view of the ablation device of FIG. 1 depicting an exemplary ablation pattern that may be achieved with the device;

FIG. 3 is a partially sectioned perspective view of the device of FIG. 1 taken from a proximal perspective;

FIG. 4 is a partially sectioned perspective view of the device of FIG. 1 taken from a distal perspective;

FIG. 5 is a cross-sectioned view of the device taken along line 5-5 of FIG. 2;

FIG. 25 is a cross-sectioned view of a directional ablation device equipped with a trocar tip configured to transmit RF energy to the surrounding tissue for cutting, cautery, or sensing, in which the electromagnetic energy is delivered using one of the cylindrical members;

FIG. 26 is a cross-sectioned view of a directional ablation device equipped with a trocar tip configured to transmit RF energy to the surrounding tissue for cutting, cautery, or sensing, in which the electromagnetic energy is delivered using a connecting wire carried by one of the cylindrical members;

FIG. 27 is a cross-sectioned view of a directional ablation device equipped with a return electrode comprising a circumscribing band positioned around the outside of the device body and electrically connected to another of the cylindrical members;

FIG. 28 is a cross-sectioned view of a directional ablation device equipped with a return electrode comprising an electrode pad positioned on the outside of the device body and electrically connected to another of the cylindrical members;

FIG. 29 is a cross-sectioned view of a directional ablation device equipped with a lumen extending through the device tip to permit fluid or drug delivery transported within one of the cylindrical members;

FIG. 30 is a cross-sectioned, perspective view of a direction ablation device equipped with a spacer into which distal end portions of the cylindrical members and antenna are received and secured; and FIG. 31 is a cross-sectioned view of the directional ablation device of FIG. 30.

Figure 6A:
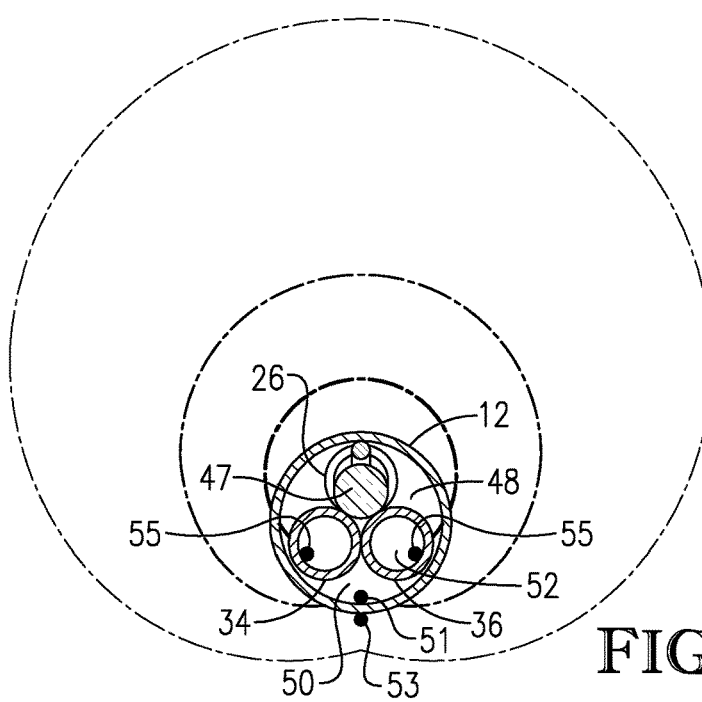
FIG. 6a is a cross-sectioned view of the device taken along line 6-6 of FIG. 2 and further depicting an exemplary ablation pattern.

While the drawings do not necessarily provide exact dimensions or tolerances for the illustrated components or structures, the drawings are to scale with respect to the relationships between the components of the structures illustrated in the drawings.

DETAILED DESCRIPTION OF THE PREFERRED EMBODIMENT

Controlling microwave radiation along an angular expanse can be achieved using a blocking/reflecting material. Many metals, such as copper, steel, titanium, and metal alloys, such as nitinol, have very high electrical conductivities, which make them very good electrical conductors. The electromagnetic field inside a good conductor reduces to 0 V/m within a very short distance past its surface (i.e., a few "skin depths"). An electromagnetic wave incident on a good conductor induces surface currents, which in turn give rise to radiation. Should the conductor be placed at an appropriate distance from the source of the incident radiation and have a favorable geometry, then the reflected electromagnetic wave would interfere with the primary source of radiation to result in radiation in a preferred direction. This effect restricts the electromagnetic power radiated in the target direction or sector.

As an alternative, antenna directivity can be created by layering dissimilar materials to create strong reflection boundaries. When electromagnetic waves are incident on material boundaries, the proportion of power transmitted or reflected, and the direction of propagation of the resulting waves depends directly on the ratio of the electric permittivity of the materials and the wave's angle of incidence on the material boundary. For instance, transitioning from a material of relatively high permittivity, such as water, to a material of much lower permittivity, such as air or plastic, results in a large fraction of the incident power being reflected, and results in more power being radiated to a desired sector.

As mentioned previously, in minimally invasive medical devices, it is desirable to constrain the size, and especially the diameter, of applicators. Thus, it can be challenging to directly apply the above concepts in their theoretically optimal arrangements. Instead, embodiments of the present invention modify and combine these concepts to achieve directivity in a minimally invasive electromagnetic radiation (e.g., microwave) ablation applicator.

Turning now to FIGS. 1-6, an embodiment of a device 10 for delivering electromagnetic energy, especially microwave energy, to a target tissue within a human or animal body is illustrated. The device comprises an elongate body 12 comprising a proximal end 14, a distal end 16, and at least one lumen 18 interconnecting the proximal and distal ends. Elongate body 12 may be formed of any suitable material for percutaneous use within a human or animal body. In one preferred embodiment, though, the elongate body is comprised of a lossless or low-loss dielectric material, such as a synthetic resin material (e.g., elastomeric or plastic materials such as polyimide, PTFE, fiberglass, and polyether ketone (PEEK) tubing), a dielectric material, or a ceramic material. While it is also within the scope of the present invention for elongate body 12 to be formed from an electrically conductive material, such as a metal (e.g., stainless steel), use of an elastomeric or plastic material reduces adhesion of ablated tissue to the device 10 during use thereby facilitating easier insertion and withdrawal of the device into and from the patient's body. In alternative configurations, elongate body 12 may be formed from conjoined sections of plastic, fiberglass, metal or other materials to achieve the desired durability or rigidity. Preferably, the overall outer diameter of the device is 0.083" (14 gauge), but the concepts described herein could be adapted for devices as small as 0.053" (17 gauge). It is understood that device 10 may have any diameter that is suitable for a given application including outer diameters greater than 14 gauge or smaller than 17 gauge.

Device 10 further comprises an antenna 20 located within lumen 18 and configured to emit electromagnetic power therefrom sufficiently strong to cause tissue ablation. Antenna 20 generally forms the terminal end of a transmission line 22 that is configured for transmitting an electromagnetic signal from a signal generator. Preferably, transmission line 22 is a coaxial cable that comprises an inner conductor 24 and an outer conductor 26 and a dielectric material 28 disposed therebetween, although other two-wire assemblies may be used. In certain embodiments, the inner conductor 24 comprises, for example, copper, silver, gold, silver-plated copper weld, or any combination thereof, and the outer conductor 26 comprises a conductive metal, for example, copper or steel. The coaxial cable may be constructed from either solid (semi-rigid) or braided central and outer conductors. In the case of a flexible device 10, outer conductor 26 may be a woven metallic (e.g., copper) shield. Preferably, the conductors are made from non-magnetic materials which may facilitate use of device 10 in an MRI machine. Otherwise, alternate materials, such as stainless steel, may be used which may impart added stiffness to device 10 thereby enhancing percutaneous usability. It is also within the scope of the present invention for more than one antenna 20 and transmission line 22 to be used with device 10. For example, device 10 may comprise two antennas 20, each extending from its own transmission line 22.

The dielectric material 28 may comprise, for example, polytetrafluoroethylene, air, polyethylene, alumina, nylon, and combinations thereof. The proximal end 30 of transmission line 22 comprises an SMA connector 23 or other structure (e.g., N-type and BNC connectors) that is suitable for connecting the transmission line to the signal generator. The distal end 32 of transmission line 22 comprises a portion of the line in which the outer conductor 26 and dielectric material 28 have been removed to expose a small length, preferably less than 1 mm, of dielectric material and a length, preferably from about 5 to about 10 mm, of inner conductor 24 to form an antenna 20. Preferably, the center conductor 26 is bent and offset near the exposed dielectric material 28 to position the antenna 20 further away from the one or more elongate cylindrical elements, which are described in greater detail below, and closer to the outer wall structure of the elongate body 12, and to achieve better impedance matching between the antenna 20 and transmission line 22. In certain embodiments, antenna 20 comprises a monopole antenna; however, other types of antenna configurations, such as dipole, slot, and helical antennas, may also be used without departing from the scope of the present invention. In addition, the exposed antenna 20 may be configured with alternative antenna bends or no bends. The monopole antenna can be coated with or covered in a dielectric material. In certain embodiments, the outer conductor 26 and dielectric material 28 can be removed flush with each other to leave no exposed dielectric material.

Figure 6B:
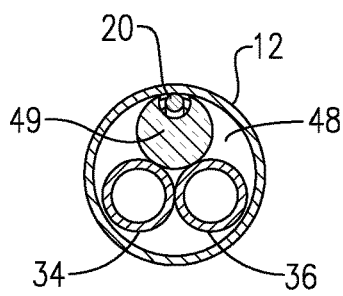
FIG. 6b is a cross-sectioned view of an alternate device configuration taken along line 6-6 of FIG. 2.
Figure 6C:
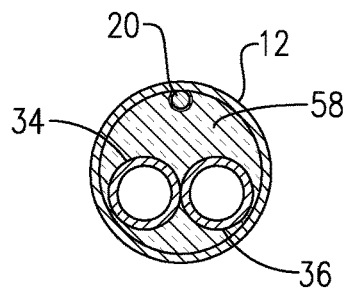
FIG. 6c is a cross-sectioned view of yet another alternate device configuration taken along line 6-6 of FIG. 2.
Figure 7:
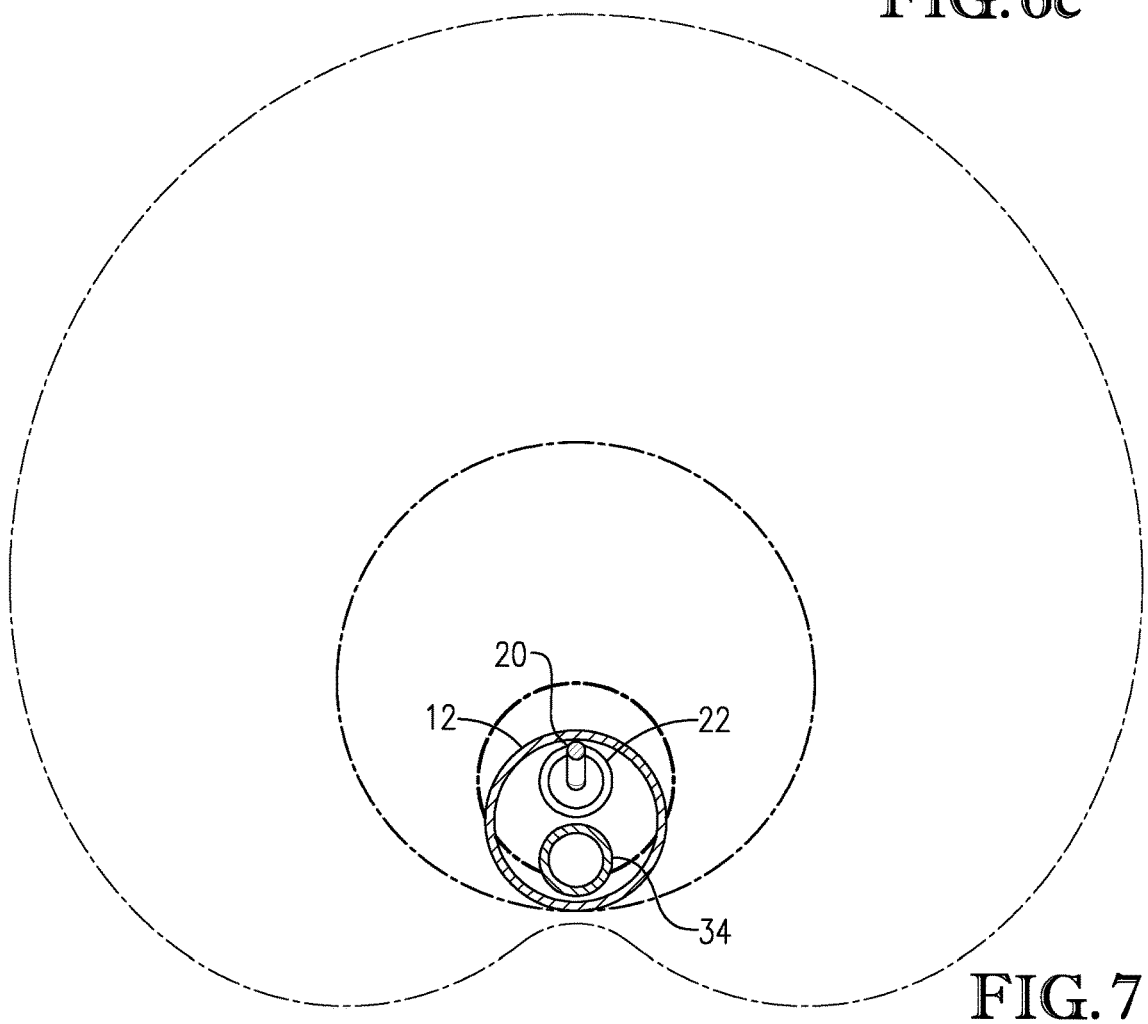
FIG. 7 is a cross-sectioned view of an alternate embodiment of the present invention in which one cylindrical member is present, and an exemplary ablation pattern produced thereby.
Figure 8:
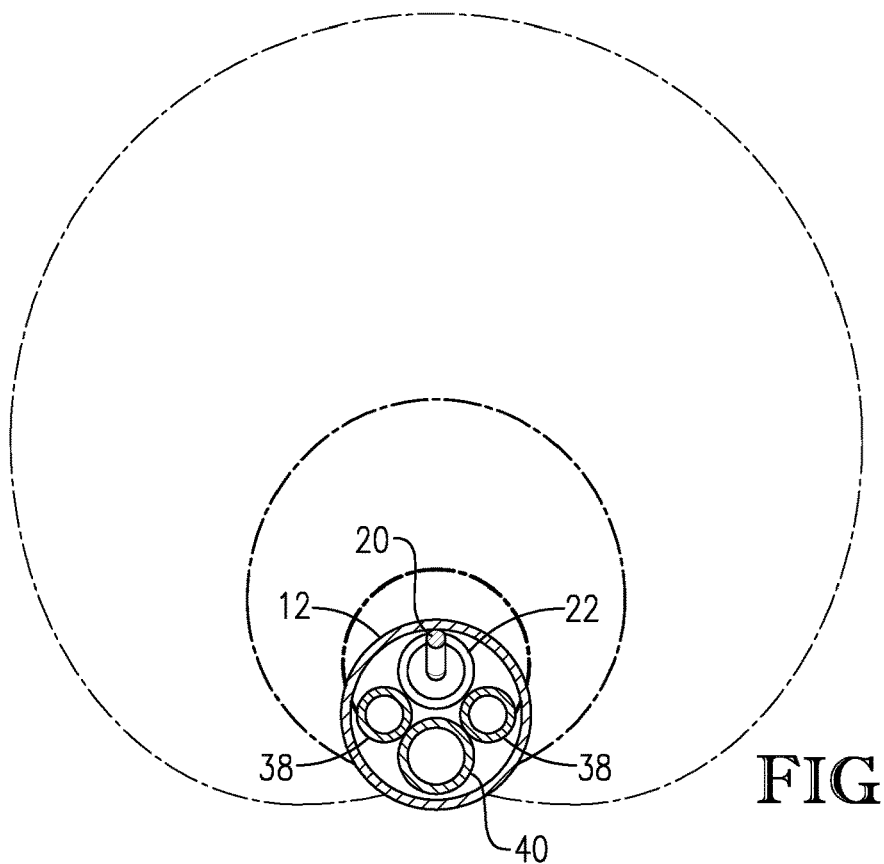
FIG. 8 is a cross-sectioned view of an alternate embodiment of the present invention in which three cylindrical members are present, and an exemplary ablation pattern produced thereby.
Figure 9:
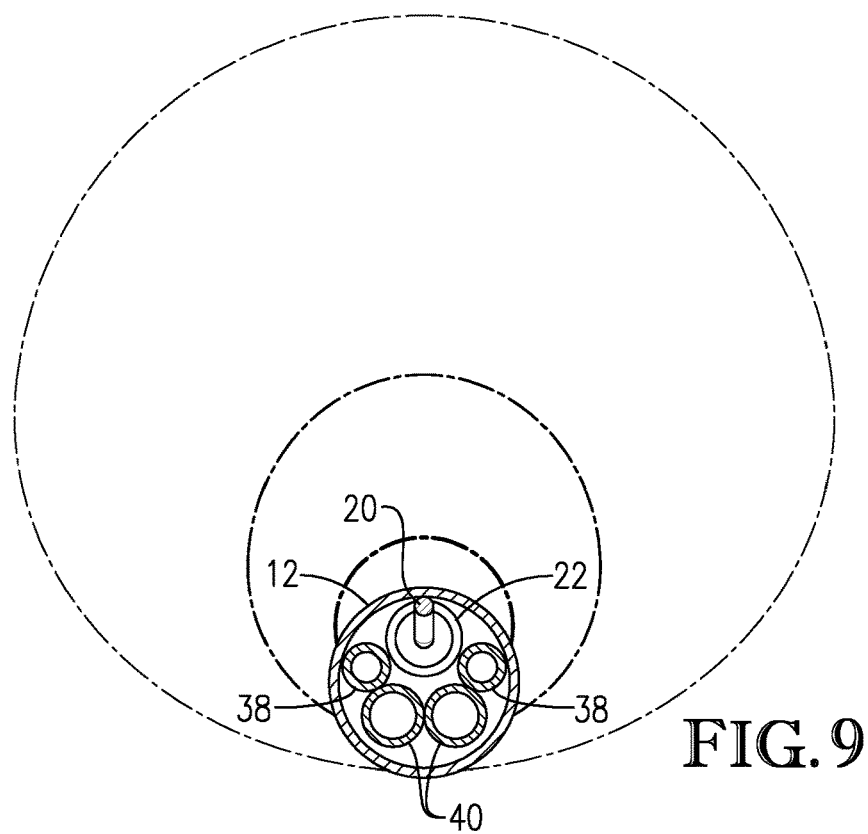
FIG. 9 is a cross-sectioned view of an alternate embodiment of the present invention in which four cylindrical members are present, and an exemplary ablation pattern produced thereby.

Device 10 further comprises at least one elongate cylindrical member 34 located within lumen 18 (i.e., the same lumen as the antenna). As illustrated, preferably device 10 comprises at least two elongate cylindrical members 34, 36. Elongate cylindrical members 34, 36 are generally disposed laterally from antenna 20, wherein the antenna 20 lies entirely outboard of the cylindrical members as opposed to residing within, being concentric with, or being at least partially carried through one of the cylindrical members. Alternate embodiments of device 10 are shown in FIGS. 7-9 in which one, three, or four more elongate cylindrical members are arranged laterally from the coaxial transmission line 22. It is also within the scope of the present invention for other numbers of elongate cylindrical members to be used in the construction of device 10 besides what is shown in the Figures. The different configurations may be used to modify the angular radiation pattern, improve mechanical performance and device rigidity, balance cooling fluid inflow and outflow area, or provide conduits for fluid delivery and auxiliary instruments. For example, FIG. 7 depicts a single elongate cylindrical member 34 disposed to the side of transmission line 22 and antenna 20. This configuration tends to generate a broader ablation pattern as indicated by the various dashed lines, which signify zones of differing radiation intensity. FIG. 8 depicts a configuration in which three elongate cylindrical members are disposed laterally from transmission line 22. In particular, the cylindrical members have different diameters, with members 38 having a smaller diameter than member 40. This configuration tends to generate a narrower ablation pattern than illustrated in FIGS. 6 and 7. FIG. 9 depicts still a further configuration in which four elongate cylindrical members are disposed laterally from transmission line 22. As illustrated, the device comprises two small-diameter members 38 positioned outboard of two larger-diameter members 40. This configuration provides an even narrower ablation pattern than those embodiments of FIGS. 6-8. By "narrow ablation pattern" it is meant that the electromagnetic energy emitted from the antenna 20 is predominantly directed toward the tissue that is closest in proximity to the antenna 20. As can be seen from FIGS. 6-9, the greater the extent that the elongate cylindrical members are positioned radially around transmission line 22, the more energy is directed in an anterior direction (i.e., toward the antenna side of the device) and the less energy is delivered to lateral and posterior tissue (i.e., to the side and opposite of the antenna).

The elongate cylindrical members can be of any cylindrical configuration, such as circular, rectangular, triangular, elliptical cylinders, and preferably at least a portion are formed of an electrically conductive material such as stainless steel, silver, copper, gold, and other metals and alloys, especially the distal portion. Alternatively, the cylindrical members may comprise a non-metallic material with the distal portion thereof bearing one or more conductive elements, such as a metal pad or band that is sputtered or electroplated thereon near the antenna. In other embodiments, the elongate cylindrical members are made from any material with high electrical conductivity ($\sigma > \sim 10^4$ S/m). The use of electrically conducting materials for the cylindrical members produces a reflecting/shielding effect, which creates areas within the device 10 or within the cylindrical members themselves that are shielded from the effects of the electromagnetic power emitted from antenna 20. As explained below, this shielding effect creates opportunities for device 10 to carry optional accessories that enhance the utility of device 10.

In certain embodiments, the elongate cylindrical members 34 may comprise a solid metal wire. However, in preferred embodiments, the elongate cylindrical members 34 may comprise hollow tubes. In those embodiments that comprise multiple elongate cylindrical members 38, 40, a combination of wires and tubes may be used, if desired.

The elongate cylindrical members 34, 36 preferably are affixed to one another such as through welding, soldering, or adhesives to form a cohesive unit having enhanced rigidity compared to the individual members. In certain embodiments, the outer conductor 26 of the transmission line 22 may also be affixed to the elongate cylindrical members 34, 36, such as through soldering or welding, thereby fusing the cylindrical members and transmission line together for added stiffness. In addition, fusing the cylindrical members and transmission line together restricts surface currents along the outer surface of the transmission line and cylindrical members, which may otherwise contribute to standing or reverse travelling electromagnetic waves. The affixing of members 34, 36 and transmission line 22 together also provides for improved or easier manufacturing and assembling of device 10 as this assembly can be slid into elongate body 12 as a single unit. In a preferred embodiment, the cylindrical members 34, 36 and transmission line 22 form a triangular arrangement in cross-section. Although, it will be appreciated that many other configurations are possible.

In certain embodiments, the cylindrical members 34, 36, specifically distal end segments thereof, are anchored in a plug 42 located toward the distal end 16. As discussed below, in other embodiments, a non-metallic spacer associated with the device distal tip can be used in place of plug 42. Preferably, plug 42 comprises a non-conductive epoxy material that is located at the very distal end of device 10 approximately 1-5 mm beyond the distal tip of antenna 20.

This allows the cylindrical members 34, 36 to provide axial rigidity through the device 10 by fixing them to both the proximal 14 and distal 16 ends.

In those embodiments in which the elongate cylindrical members 34, 36 comprise tubes, one or more of the tubes can be used to provide either an inflow or outflow path for circulating a cooling fluid within the device 10 to dissipate heat generated during operation. A small notch 44 is cut in each tube slightly proximal from the distal plug 42 to provide a path for the circulating cooling fluid to enter or exit the tubes. Note, a plurality of notches or holes spaced about the circumference of each tube may also be provided instead of a single notch. The notches may be configured to face the same or different directions within lumen 18. For example, the notches in cylindrical member 34, 36 may both face the anterior of the device, may both face away from the anterior of the device, or one notch may face the anterior and one notch away from the anterior of the device in order to balance the flow of cooling fluid through the device. Alternatively, the tubes may be configured to terminate prior to insertion into the distal plug 42 with the flow path for the cooling fluid being provided through the open ends of the tubes. The distal portions of the cylindrical members 34, 36 may be cut, shaped, or otherwise modified to form a variety of alternate shapes. For example, the circular cross section of the cylindrical members 34, 36 may be cut in half and removed from a length of the distal end of the cylindrical member, resulting in a concave/convex structure near the antenna as a means to alter performance characteristics or facilitate smaller diameter design variants. Alternatively, the cylindrical member can be flattened or bent along a portion of the distal end. Thus, the cylindrical members need not be of constant cross-sectional profile along their entire lengths. The distal end of the device 10 can be terminated in a trocar tip 46 or other type of pointed tip for easier insertion into tissue.

As previously mentioned, water is a preferred cooling fluid for circulation within the device 10. With reference FIGS. 1-5, the void 48 within lumen 18 between the elongate body 12 and the assembly comprising the elongate cylindrical members 34, 36 and the transmission line 22 forms part of the out/inflow path for circulating water (see, directional arrows). In this embodiment, the antenna 20 is unsupported at its distal end and is surrounded by circulating water. The high relative permittivity of the surrounding water contributes to proper antenna impedance matching. In alternate configurations, the distal and/or proximal ends of the antenna 20 may be held in place by epoxy or some other material. This may allow for improved manufacturability or performance consistency. Since water also has an appreciable electrical conductivity, alternate configurations may fill some or all the void 48 between the antenna 20 and the cylindrical members 34, 36 with a low-loss material with high dielectric constant such as the ceramic materials alumina and $TiO_2$. The cylindrical members may be notched at some location proximal to the antenna 20 (in certain embodiments approximately 2 mm from the base of antenna 20) to allow return flow in design variants where the entire space inside the elongate body 12 is filled with low-loss material to surround the antenna element and cylindrical members 34, 36. This low loss material, which may comprise $TiO_2$, may also be molded to, or otherwise used to fully encapsulate the antenna 20 and cylindrical members where the low-loss material also forms the part of the outer surface of the applicator for a length near the distal tip 46 of the device 10. The inclusion of low-loss materials near the antenna 20 would limit microwave absorption losses inside the device 20, allowing more microwave energy to reach outside the device 10 and produce larger ablation zones in the target tissue. Furthermore, since microwave loss within the device 20 raises the device's internal temperature, including alternative low-loss material may enable higher applicator operational power levels. One practical example of this configuration is a small diameter $TiO_2$ cylinder 47 positioned between the antenna 20 and the cylindrical members 34, 36 to displace lossy water in that region. See, e.g., FIGS. 2 and 6a. Note, cylinder 47 is optional and is not required to be present in every embodiment of the invention. If a dielectric other than water is used around antenna 20, it should have a similarly large dielectric constant as water (e.g., $TiO_2$), and alternate cooling fluids can be used including saline, FLUORINERT, liquid chlorodifluoromethane, nitrous oxide, nitrogen, carbon dioxide and air. FIG. 6b depicts another variation of this concept in which antennal 20 is at least partially embedded within or surrounded by a $TiO_2$ cylindrical element 49. FIG. 6c illustrates a further variation of this concept in which a portion of void 48 and space 50 is filled with $TiO_2$ material 58 along the length of antenna 20. Note, in this embodiment, circulation of a cooling fluid may need to occur entirely within cylindrical members 34, 36, at least in the region of antenna 20.

Because cylindrical members 34, 36 are electrically conductive, they are highly effective at shielding regions both interior and exterior of device 10 from the electromagnetic power emitted by antenna 20. These shielded regions are useful for placement of at least one sensor that is configured to detect an operating condition of the device 10 or a condition associated with the body in which the target tissue is located. In one embodiment, the space 50 between the elongate body 12 and cylindrical members 34, 36 opposite the transmission line 22 can be used as a shielded location for the addition of at least one sensor 51. See, FIG. 6. A sensor 53 may also be adhered to that portion of the exterior surface of elongate body 12 that is shielded by cylindrical members 34, 36.

In one embodiment, the at least one sensor is a temperature sensor, and preferably, a thermocouple. When placed within space 50, thermocouple temperature sensors 51 can be used to monitor internal temperatures of device 10 as a safety or feedback mechanism. When adhered to the shielded exterior surface of elongate body 12, this temperature sensor 53, or an additional sensor, can be used as a real-time safety system to alert the user to unintended heating in an undesired sector of tissue. A sensor 55 (e.g., a thermocouple) may also be included within the lumen 52 of the metallic tubes 34, 36, which is well shielded from the electromagnetic power emitted from antenna 20. When a thermocouple sensor 55 is used in this fashion, the ends of the thermocouple(s) may be anchored into the same distal plug 42 as the cylindrical members 34, 36 and be configured to measure real time temperature at any point around the circumference of device 10. Electromagnetic shielding is important for thermocouple wires because they are also metallic and any microwave radiation reaching them would induce heating and cause erroneous readings.

In still further embodiments, one or more of the metallic tubes 34, 36 could be used as a conductor for transmission of radio frequency energy to a conductive device tip. This may be used for RF ablation, cutting, or cautery.

FIGS. 25-27 depict further embodiments of device 10 that can be configured for RF cutting or cautery, or for sensing a condition associated with the tissue in which the device 10 is in contact, such as tissue impedance. Turning first to FIGS. 25 and 26, two embodiments of device 10 are illustrated in which device 10 is equipped with a conductive trocar tip 46. In the embodiment of FIG. 25, electromagnetic energy is delivered to tip 46 by conductive cylindrical member 34. As can be seen, cylindrical member 34 extends through plug 42 and is electrically coupled to tip 46 at interface 122. The embodiment of FIG. 26 is similarly configured, however, electromagnetic energy is delivered to tip 46 by a connecting wire 124, which is shown as being carried by cylindrical member 34, although this need not always be the case. In these embodiments, tip 46 can be used to cut or cauterize tissue through use of RF energy, or tip 46 can be configured to transmit an electrical signal, via cylindrical member 34 or connecting wire 124, that is indicative of a condition associated with the surrounding tissue, such as tissue impedance.

As the tip 46 acts as a first electrode of the cutting, cautery, or sensing system, a second electrode must be provided as the return path for the signal. FIGS. 27 and 28 depict two alternative embodiments for placement and connection of this second electrode. The embodiment of FIG. 27 comprises a circumscribing electrode band 124 that is positioned on the outer surface of elongate body 12. Band 124 is electrically connected to cylindrical member 36 by connector 128. The embodiment of FIG. 28 comprises an electrode pad 126 that is positioned on the outer surface of elongate body 12 and is electrically connected to cylindrical 36 by connector 130. As yet a further alternative, the return electrode need not be a part of device 10 at all, but rather could be in the form of an external grounding pad (not shown) that is adhered to the patient's skin.

In alternate embodiments, one or more of the metallic tubes 34, 36 could be extended all the way through the distal plug 42 and/or tip 46 and be used as a conduit for fluid/drug delivery to the patient's body. Such an embodiment is illustrated in FIG. 29. As can be seen, tube 34 comprises a distal beveled edge that lies flush with the outer surface of tip 46 and communicates the lumen of tube 34 with the exterior of device 10. A number of alterations to this embodiment are readily envisioned without departing from the overall scope of the invention. For example, the tip 46 may be formed with a lumen that communicates with the lumen of tube 34, but tube 34 does not extend into or all the way through the tip's lumen.

In yet further embodiments, one or more of the metallic tubes 34, 36 could be extended beyond the distal plug 42 and electrically connected to a sensor (not shown) mounted on the applicator surface to monitor target tissue impedance or other electrical property. However, as noted above, the device tip 46 can also be configured to operate as a sensor or electrical contact without necessitating a further external sensor be added to the device.

FIGS. 30 and 31 depict an alternate embodiment of a directional ablation device 134 in accordance with the present invention. As with certain other embodiments described herein, device 134 comprises an elongate body 136 defining a lumen 138 into which a transmission line 140, antenna 142, and cylindrical members 144, 146 are received. The distal end of device 134 terminates in a trocar tip 148 that is secured to the distal end of body 136. Each of cylindrical members 144, 146 comprise a plurality of orifices 150 that communicate the interior of each cylindrical member with lumen 138.

The distal end 152 of each cylindrical member 144, 146 is seated within a spacer 154 that is secured to tip 148. In preferred embodiments, spacer 154 is non-conductive (e.g., formed from a rigid plastic or other insulative material) so as to electrically isolate cylindrical members 144, 146 from tip 148, although this need not always be the case. In the embodiment illustrated, spacer comprises a projection 156 that is received within a bore 158 formed in tip 148. Thus, spacer 154 provides a rigid connection between the distal ends 152 of the cylindrical members and the rigid tip 148. In alternative embodiments, spacer 154 and tip 148 may be unitary (i.e., formed from a single piece, especially if tip 148 can be formed from a rigid, non-conductive material) and need not comprise separate components. However, the use of separate, but connectable, components may be advantageous from a manufacturing perspective.

Also, in one or more embodiments, the distal end 160 of antenna 142 may also be received within spacer 154, which supports distal end 160 and maintains the position of antenna 142 relative to cylindrical members 144, 146 ensuring the appropriate antenna impedance matching. It is noted that cylindrical members 144, 146 and/or antenna 142 can be frictionally secured to spacer 154 or secured thereto with an adhesive, such as an epoxy.

Figure 10:
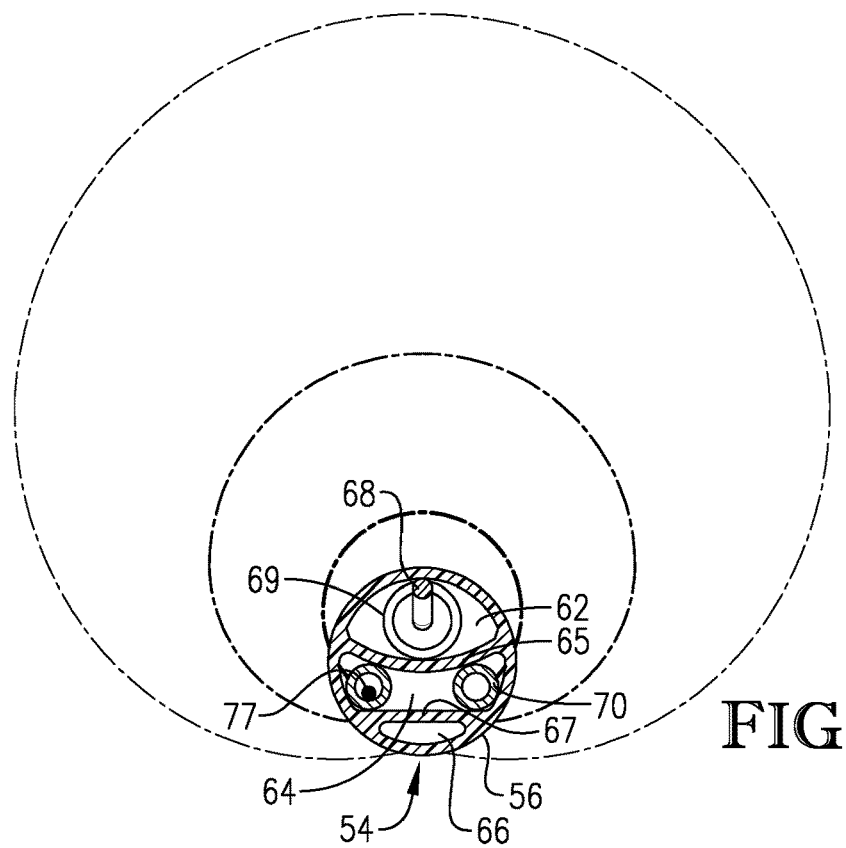
FIG. 10 is a cross-sectioned view of a multi-lumen device in accordance with an alternate embodiment of the present invention, and an exemplary ablation pattern produced thereby.
Figure 11:
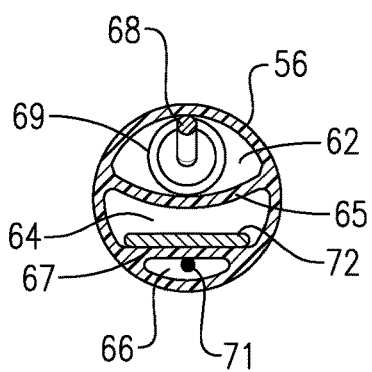
FIG. 11 is a cross-sectioned view of a multi-lumen device comprising a flat reflector element.

Turning to FIG. 10, another embodiment of a device 54 for delivering electromagnetic energy to a target tissue is illustrated. Device 54 comprises an elongate body 56 formed from a synthetic resin material. Device 54 comprises a proximal end, a distal end, and at least two lumens 62, 64 interconnecting the proximal and distal ends. As illustrated device 54 further comprises a third lumen 66, but this need not always be the case. Moreover, it is within the scope of the present invention for device 54 to comprise any number of lumens, such as two, three, four, five, or six. The various lumens formed within elongate body 56 are separated by wall structures that extend between the proximal and distal ends. For example, lumen 62 is separated from lumen 64 by wall 65. Preferably, wall 65 is arcuate in shape having a concavo-convex configuration, although it is within the scope of the present invention for wall 65 to be of any suitable configuration. Likewise, lumen 64 is separated from lumen 66 by a wall 67 that is preferably flat but may be of any suitable configuration.

In certain embodiments, the multi-lumen elongate body 56 comprises a synthetic resin material that can be extruded into the desired configuration, such as PEEK, but it is within the scope of the present invention for elongate body 56 to be formed from any material that is electromagnetically transparent at microwave frequencies.

Lumen 62 preferably is set against one side of the outer wall of elongate body 56 and has a height that is large enough to accommodate a coaxial transmission line 69. Preferably, lumen 62 is sized to hold transmission line 69 snugly between the outer wall of elongate body 56 and wall 65. An antenna 68 is located within lumen 62 and is configured to emit electromagnetic energy therefrom sufficiently strong to cause tissue ablation. Antenna 68 may be configured similarly to antenna 20 discussed above.

Device 54 comprises at least one electrically conductive member (also referred to herein as a "reflective member") located within lumen 64 (i.e., a different lumen than that in which antenna 68 is located) that is operable to at least partially reflect microwave energy and/or at least shield a portion of the device and/or patient's tissue from microwave energy. The at least one reflective member may comprise any one of several configurations. For example, as depicted in FIG. 10, the at least one reflective member may comprise a cylindrical member 70, which may be a wire or tube as discussed above. Preferably, the at least one reflective member frictionally engages dividing wall 65 and at least one other wall surface defining lumen 66 (e.g., the elongate body outer wall and/or wall 67) in which the at least one reflective member is received.

As illustrated in FIGS. 11-14, however, the reflective member may comprise a flat reflector 72 or concavo-convex reflector (collectively, 74). Preferably, the reflective member is metallic and extends between the proximal and distal ends of elongate body 56, although it is within the scope of the present invention for the at least one reflective member to be located primarily toward the distal section of device 54 near antenna 68.

Figure 12:
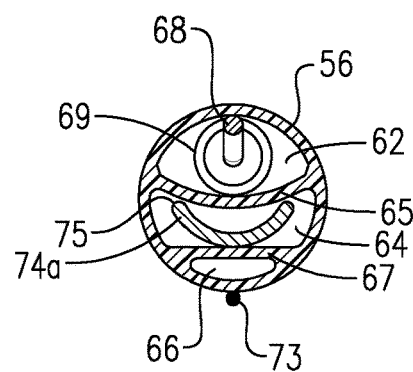
FIG. 12 is a cross-sectioned view of a multi-lumen device comprising a narrow, curved reflector element with the concave surface facing the antenna.
Figure 13:
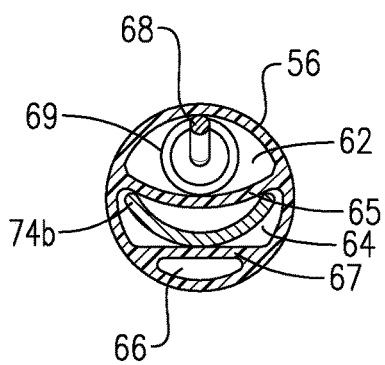
FIG. 13 is a cross-sectioned view of a multi-lumen device comprising a wide, curved reflector element with the concave surface facing the antenna.
Figure 14:
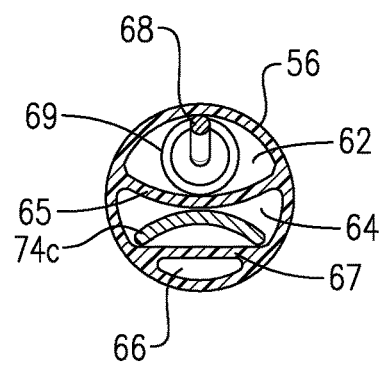
FIG. 14 is a cross-sectioned view of a multi-lumen device comprising a curved reflector element with the convex surface facing the antenna.

The embodiments of FIGS. 12-14 comprise a concavo-convex reflector 74*a-c*. The embodiment of FIG. 12 utilizes a narrow reflector 74*a*, whereas the embodiment of FIG. 13 utilizes a wider reflector 74*b* having a greater radius of curvature. In the embodiments of FIGS. 12 and 13, the reflectors 74*a,b* are oriented with the concave surface in facing relationship to the antenna 68 creating, in effect, a parabolic reflector tending to focus the microwave energy toward the anterior of the device. In the embodiment of FIG. 14, the reflector 74*c* is oriented with the convex surface in facing relationship to the antenna 68. In this embodiment, the angle of microwave energy dispersion and the resulting ablation shape may be somewhat different than that experienced with reflectors 74*a,b*.

Device 54, like device 10, is configured to permit circulation of a cooling fluid (e.g., water) therethrough. For example, the cooling fluid may be introduced into the device via lumen 64. The cooling fluid may flow through the lumen itself, or it may flow through the one or more cylindrical members 70 positioned within the lumen 64. Toward the distal end 60, wall 65 may have a short segment (e.g., 0.5-10 mm) removed to allow a return path for the cooling fluid through lumen 62. Wall 65 also provides a high to low permittivity (water to plastic) material interface, which may cause some of the microwave energy to reflect to the desired sector for tissue ablation.

As illustrated in FIG. 10, device 54 comprises at least two reflective members, here cylindrical members 70, that fit snugly between the outer wall of elongate body 56 and walls 65, 67. As with device 10, the at least one reflective member of device 54 can be fixed in a plug that is used to seal the distal end of the device. This plug can be configured similarly to plug 42 described above and may provide added strength and rigidity to device 54.

Lumen 66 is comprised of the area defined by the outer wall of elongate body 56 and wall 67. In certain embodiments, lumen 66 may be filled with air to provide a water, plastic, air interface reflection boundary to enhance the directivity of the applicator. Furthermore, it is possible to configure device 54 so that lumen 66 is shielded from microwave radiation by the at least one reflective member allowing for the routing of at least one sensor configured to detect an operating condition of the device or a condition associated with the body in which the target tissue is located. In certain embodiments, the at least one sensor 71 comprises a thermocouple routed in lumen 66. See, e.g., FIG. 11. In other embodiments, a temperature sensor 73 may be positioned on the back (shielded) side of the device 54. This temperature sensor may be used as a real-time safety system to alert the user to unintended heating in the undesired sector. An additional sensor (not shown) could be used to monitor device internal temperatures as a safety or feedback mechanism. If the one or more reflective members comprise tubes 70, additional sets of thermocouple wires 77 could be routed through these tubes as described above.

In other embodiments, lumen 66 can be used as an additional cooling fluid closed-flow channel to enhance indirect cooling in the backwards sector. Lumen 66 may also be opened at the distal end to allow open-system cooling flow to the backward sector. Open flow from lumen 66 could also be used for drug delivery, either to the backward sector or to the forward sector if the device 54 is rotated 180 degrees prior to or following ablation treatment.

In an alternative configuration, the one or more elongate cylindrical members 70 can be extended all the way through the distal plug and device tip to be used for fluid/drug delivery to the patient's body.

In still further embodiments, one or more of the elongate cylindrical members 70 could be used as a conductor for transmission of radio frequency energy to a conductive device tip. This may be used for RF ablation, cutting, or cautery.

In yet further embodiments, one or more of the elongate cylindrical members 70 could be extended beyond the distal plug and electrically connected to a sensor (not shown) mounted on the applicator surface to monitor target tissue impedance or other electrical property.

Figure 15:
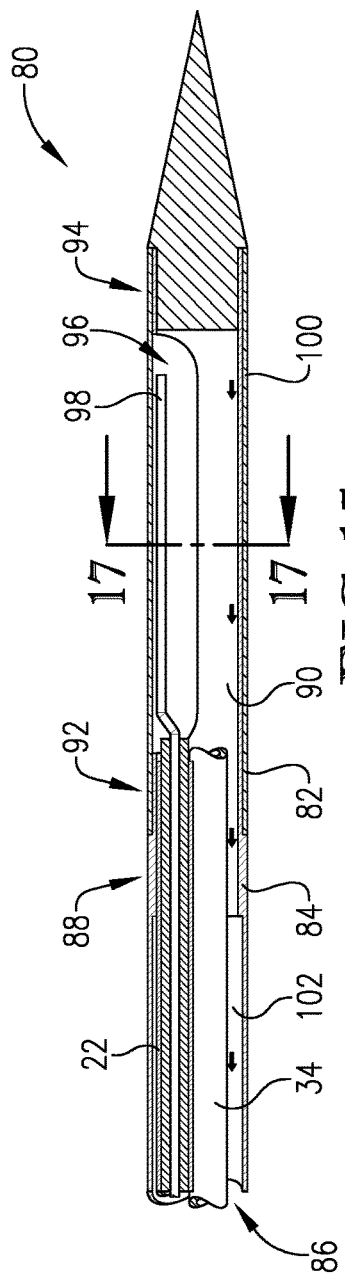
FIG. 15 is a partial cross-sectioned view of an alternate embodiment of an ablation device formed with concentric tubular members.
Figure 16:
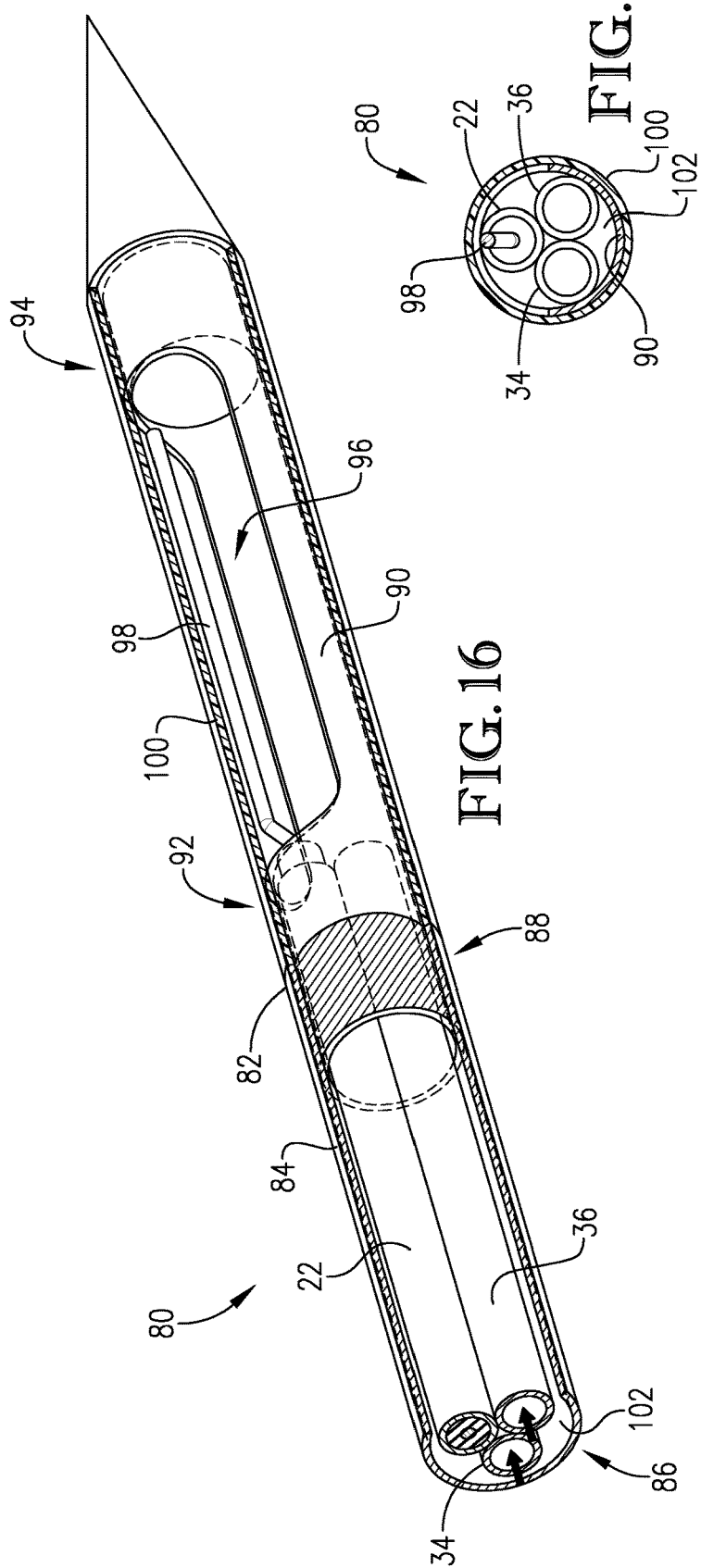
FIG. 16 is a sectioned perspective view of the device of FIG. 11.
Figure 17:
FIG. 17 is a cross-sectioned view of the device taken along line 13-13 of FIG. 11.

FIGS. 15-17 depict another embodiment of a device 80 for delivering electromagnetic energy to a target tissue. Device 80 is configured such that elongate body 82 comprises an outer tubular member 84 having a proximal end 86 and a distal end 88. Elongate body 82 further comprises an inner tubular member 90 having a proximal end 92 and a distal end 94. The proximal end 92 of the inner tubular member 90 is received through the distal end 88 of the outer tubular member 84. Therefore, inner tubular member 90 has an outer diameter that is approximately the same or slightly less than the inner diameter of the outer tubular member 84. Preferably, tubular members 84, 90 are metallic and may comprise the same materials used for cylindrical members 34-40 described above. However, it is within the scope of the present invention for tubular members 84, 90 to be formed from a microwave transparent material such as those described above for elongate body 12.

The inner tubular member 90 comprises a window section 96 formed therein that is configured to permit transmission of the electromagnetic power emitted from the antenna 98. In preferred embodiments, the window section 96 is formed by removing a section of the inner tubular member 90 (preferably 10-15 mm in length) corresponding to the desired dimensions for the window section. Device 80 further comprises an electromagnetically transparent sleeve 100 that is positioned around at least a portion of the inner tubular member 90 in covering relationship to the window section 96. Thus, sleeve 100 seals window section 96 and prevents direct communication of lumen 102 with the exterior of device 80. Sleeve 100 can be made from any number of non-metallic materials such as polyimide, PEEK, or ceramic. Preferably, sleeve 100 has a diameter that is approximate to the diameter of outer tubular member 84. The inner tubular member 90 may function, then, as a reflector directing the electromagnetic power emitted by antenna 98 in a forward direction toward window section 96.

The other components and features of device 80 can be configured similarly to those of device 10. However, it is also within the scope of the present invention to construct device 80 using a concentric tube design whereby the antenna extends from a transmission line that is run through the lumen of a tube through which a cooling fluid may circulate. U.S. Patent Application Publication No. 2017/

0265940, which is incorporated by reference herein in its entirety, illustrates an exemplary concentric flow tube design.

Figure 18:
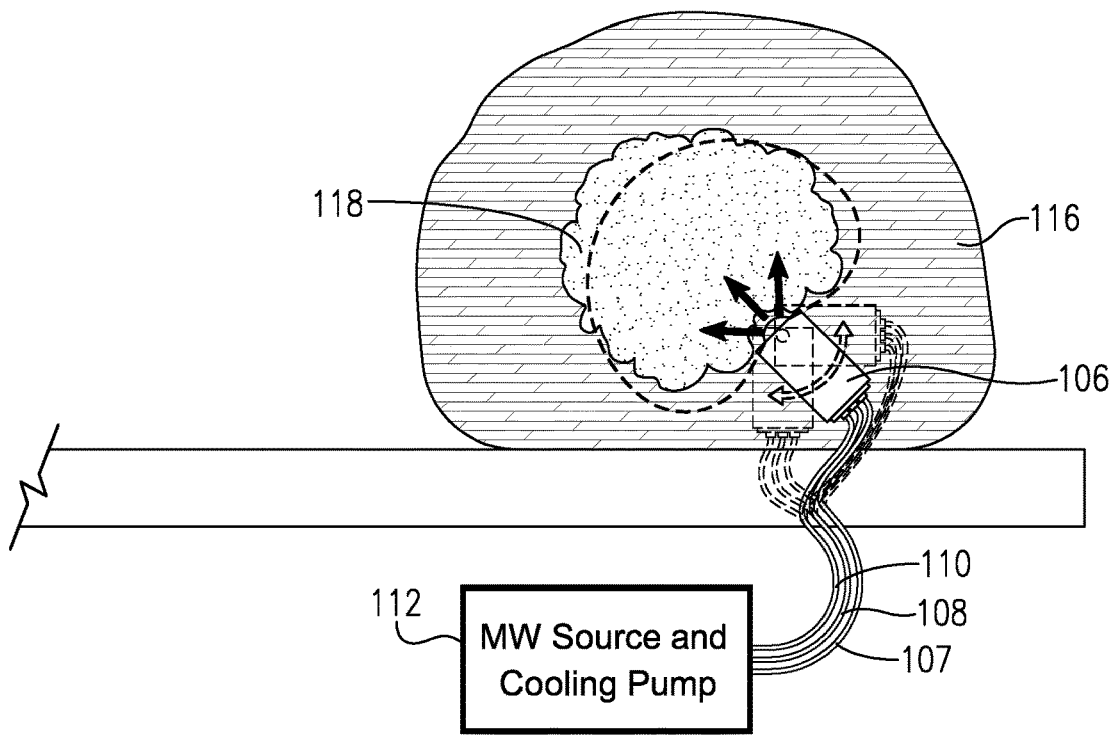
FIG. 18 is a schematic illustration of a device according to the present invention equipped with a swivel connector accessory.
Figure 19:
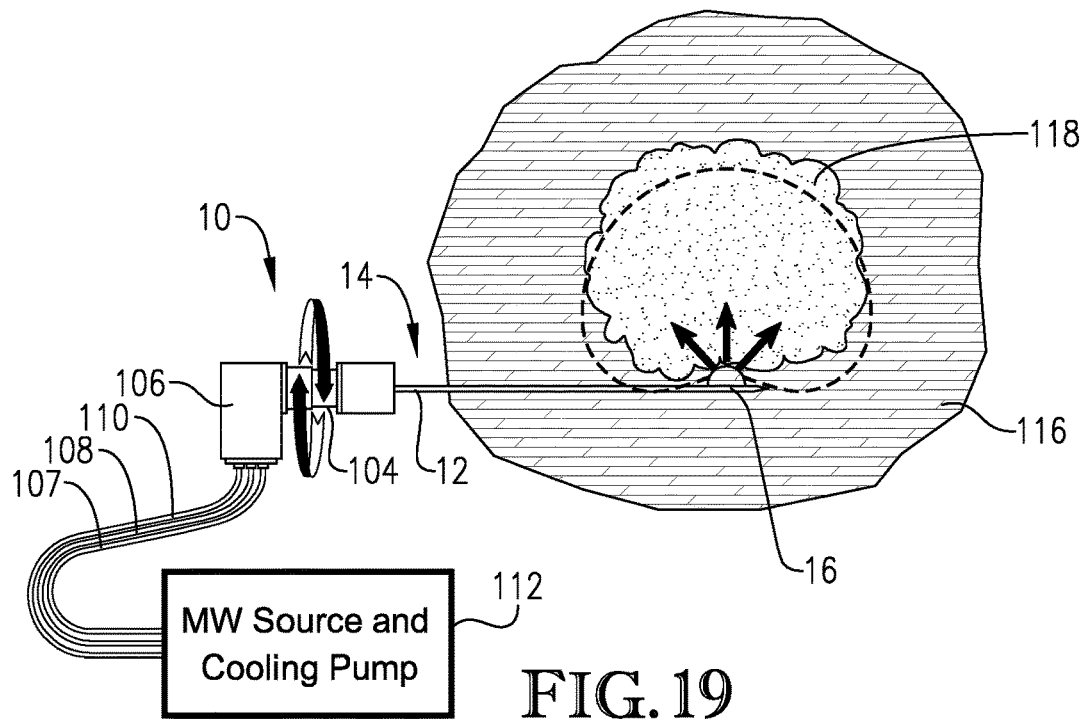
FIG. 19 is a further schematic illustration of a device according to the present invention equipped with a swivel connector accessory.

Several peripheral accessories may be used with the devices described herein to improve the functionality thereof. The peripheral accessories described herein can be used individually or in conjunction with each other as the application demands. FIGS. 18 and 19 schematically illustrates device 10 wherein the device comprises a swivel connector 104 coupled to the proximal end 14 of the elongate body 12 and to a base portion 106 of the device. The base portion 106 is configured to receive microwave transmission line 107 and cooling fluid flow lines 108, 110 from a source of electromagnetic power and/or a pump (collectively 112) for circulating a cooling fluid within the device. The swivel connector 104 permits free axial rotation of the base portion 106 relative to the elongate body 12. Thus, once the distal end 16 of the device 10 is positioned within the patient's body, the effects of rotational torque attributable to the weight of transmission line 107 and cooling fluid flow lines 108, 110, which may cause the position/aim of device 10 to drift during use, can be avoided. As such, the risk of thermal damage to unintended areas within the patient's body is lessened.

Figure 20:
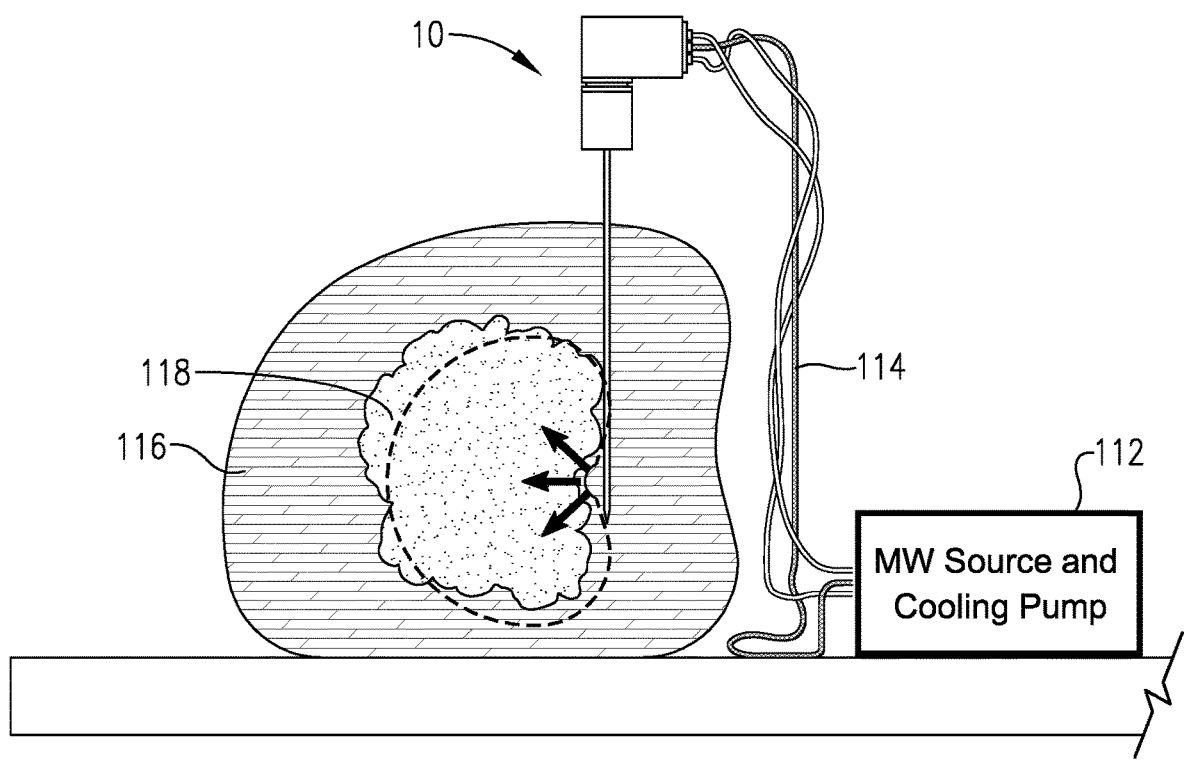
FIG. 20 is a schematic illustration of a device according to the present invention equipped with a formable cable capable of supporting the weight of the device.

FIG. 20 schematically illustrates another peripheral accessory that may be used with the devices described herein. In particular, a formable transmission cable 114 can be used to interconnect the source of electromagnetic power and/or pump 112. Formable cable 114 is a semi-rigid coaxial cable that is configured to be hand-formed into a desired shape and retain that shape while supporting the weight of the device 10. In certain embodiments, formable cable 114 can be used as a stand for device 10 thereby maintain the device in place during an ablation procedure or moving the patient in or out of a CT for imaging. As illustrated, the formable cable 114 is operably connected to base portion 106, which is coupled with the proximal end 14 of elongate body 12. Formable transmission cable 114 is the operably connected to source 112. Formable transmission cable 114 is configured to freely support the weight of the elongate body 12 and base portion 106 without additional assistance.

As indicated above, an electromagnetic power source 112 is used to generate and transmit the desired microwave power to device 10. Electromagnetic power source 112 may include a microwave signal generator, and optionally a DC power supply, a power amplifier, and a power monitor. In certain embodiments, the frequencies generated by the signal generator are similar to those that are associated with the frequencies typically used to heat water. In particularly preferred embodiments, the frequencies generated range from about 800 MHz to 6 GHz, from about 900 MHz to about 5 GHz, or from about 1 GHz to about 3 GHz, or about 915 MHz or about 2.45 GHz.

The operation of device 10 and its various peripheral accessories may be monitored and controlled by a microprocessor, such as a personal computer or a handheld device. Alternatively, the operation of device 10 and its peripheral accessories can be monitored and controlled by a user interface and control system that is integral with the electromagnetic power source 112.

The devices described herein can be used in several applications for ablating tissue, such as a tumor, nerve, or other tissue, within the body of a human or animal. Generally, the device is inserted into the body containing the tissue to be ablated. Insertion of the device may be carried out percutaneously, particularly when the device 10 is equipped with a trocar tip 46 to create an opening in the skin. The device may also be used in open surgery or inserted laparoscopically, such as through an incision and/or through a trocar that has been previously inserted into the patient's body. In addition, in certain embodiments if the antenna is incorporated onto the distal end of a flexible cable assembly, the device may be used endoscopically or used within a body lumen (endo-luminally) directly such as within a vein or artery (endo-vascularly), or bronchoscopically. Once inside the patient's body, the device 10, and particularly the device antenna 20, is positioned adjacent to the tissue to be ablated, such into an organ in which a tumor is located. In preferred embodiments, the antenna 20 is positioned so that the tissue to be ablated resides substantially to one side of the antenna, rather than being medially positioned within the tissue. The device 10 then is activated thereby causing the antenna to emit electromagnetic radiation, preferably microwave radiation, that is sufficiently strong to cause ablation of the tissue.

The directional nature of device 10 provides angular control of the ablation pattern thereby making possible several applications that conventional, non-directional devices have not been suited to perform. Conventional, non-directional devices must generally be inserted into the center of the target tissue as the ablative energy will be radiated outwardly in a substantially symmetrical pattern. However, this can lead to problems when the tissue to be ablated is irregularly shaped, or the center of the tissue is not easily accessible to the device. Accordingly, the directional devices according to embodiments of the present invention make alternate ablations schemes possible.

Figure 21:
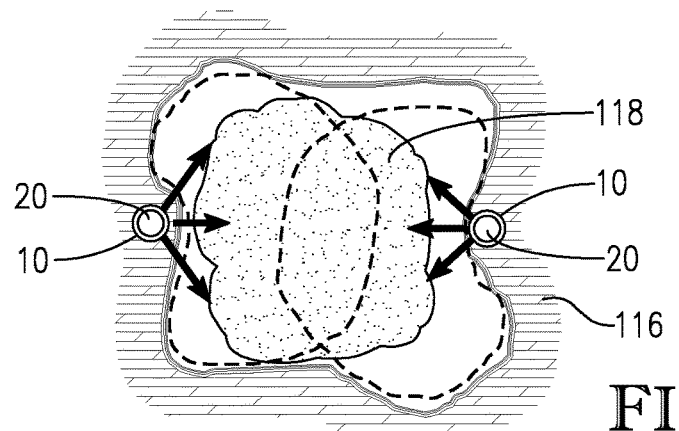
FIG. 21 is a schematic illustration of an "outside-in" ablation scheme employing two devices according to the present invention.
Figure 22:
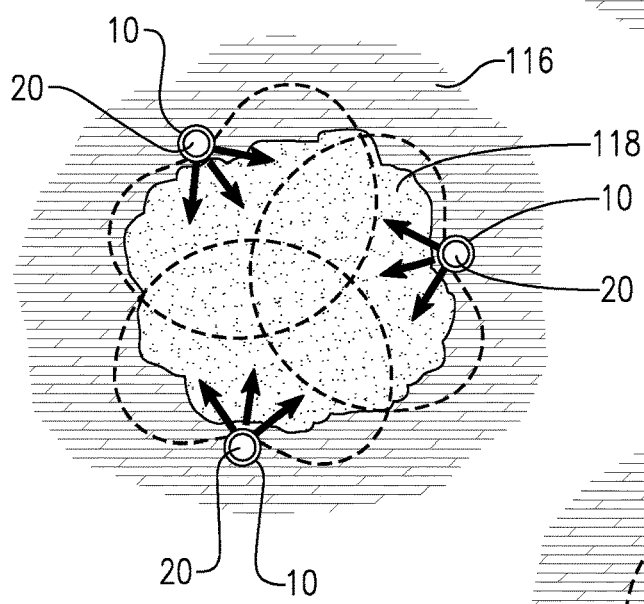
FIG. 22 is a schematic illustration of an "outside-in" ablation scheme employing three devices according to the present invention.

For example, FIGS. 21 and 22 depict and "outside-in" approach that can be used for the thermal ablation of a target tissue. In this approach, one or more devices 10, preferably two or three, can be inserted into the body 116 of a patient and positioned adjacent to a target tissue, such as a tumor 118, but without penetrating the target tissue. Activating device 10, which thereby causes antenna 20 to emit ablative microwave radiation into the tissue 118 in a specific directional pattern (indicated by the dashed lines), effects ablation from the outer margins of the tissue inwardly toward the center of the tissue. The devices may be energized to operate simultaneously (i.e., all devices radiating microwave radiation continuously during an ablation procedure), or with power cycled between the devices. For example, considering the dual device approach illustrated in FIG. 21, power may be supplied to one device 10 for a period of time (e.g., 5 seconds) but not the other device. Next, the power to the first device would be cut off, and power supplied to the second device for a similar or different period of time as the situation demands. Power would then be interleaved between the devices throughout the ablation procedure. Further, depending upon the geometry of the target tissue, device position, and antenna orientation, the power supplied to each device and duration of each ablation step needs not be equal. Thus, over-ablation of the tissue adjacent to the target tissue can be limited, and backward heating from the device can be minimized.

Figure 23:
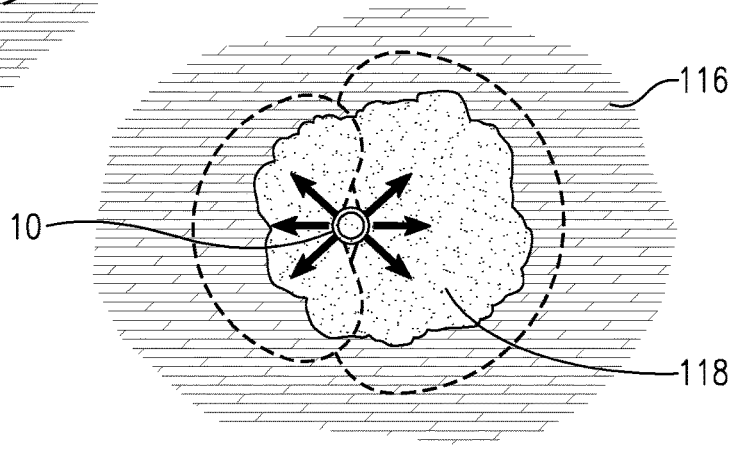
FIG. 23 is a schematic illustration of a "sector-sweep" ablation scheme using a device according to the present invention.

Another ablation scheme that can be performed is a "sector-sweep" approach as illustrated in FIG. 23. In this treatment technique, the central axis of the target is not accessible for percutaneous placement of an omni-directional ablation applicator, or the target has a non-symmetrical shape. According to this embodiment of the invention, a directional microwave applicating device 10, such as those described herein, is inserted into the target 118 off-axis, used to apply one power level using one power/time setting in one direction to a portion of the tumor, and then rotated (preferably without removing the device from the target) to apply a different power level with a different time/power settings in one or more other directions to a different portion of the tumor. This scheme is depicted by the asymmetric ablation patterns shown with dashed lines. This scheme allows for complete ablation of symmetrical tumors that cannot be accessed along the central axis or other tumors that do not have a symmetric shape. This method could also be used for selective retreatment procedures within the same target zones that show viability post initial ablation.

Figure 24:
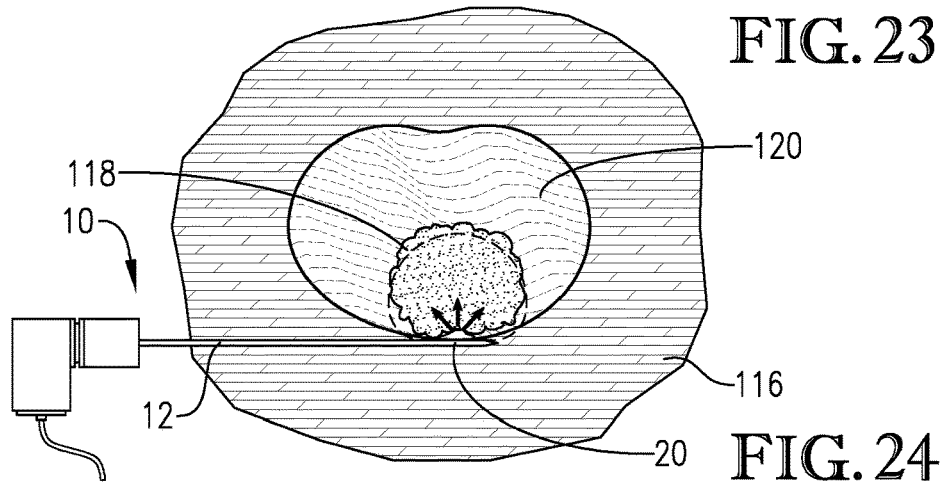
FIG. 24 is a schematic illustration of an ablation scheme using a device according to the present invention in which a tumor located within an organ is ablated without the device entering the organ.

FIG. 24 illustrates still a further ablation scheme according to an embodiment of the present invention, which may be referred to as surface ablation. In this scheme, device 10 is inserted into the body 116 of a patient. The portion of elongate body 12 containing the antenna 20 is positioned adjacent to an organ 120, such as a liver or pancreas. Note, in this embodiment, the device 10 is positioned in direct contact with organ 120, preferably with the assistance of CT or ultrasound guidance, but does not penetrate or extend inside it. This method is particularly useful when the tumor 118 to be ablated resides near or extends inwardly from an outer surface of the organ 120. The ablation pattern (dashed lines) created by antenna 20 can be configured to ablate substantially the entire target tissue while causing minimal thermal damage to surrounding healthy tissue. In addition, further trauma to the organ 120 is avoided because device 10 is not inserted into the organ.

Certain embodiments of the present invention can be used to perform cutting or cauterizing of tissue located within the body, especially by delivering radio frequency energy from the device tip 46 as described above. This may be useful in minimizing bleeding that may occur during applicator placement or removal that may obscure CT or ultrasound image guidance. Also, as described above, certain devices according to the present invention can be used to sense an electrical characteristic of a tissue located within the body, such as tissue impedance, which may be useful for treatment planning or determining treatment endpoint.

It is understood that the foregoing descriptions are meant to be illustrative of the preferred features and concepts of the present invention and should not be taken as limiting upon the scope thereof. In addition, any of the individual features and concepts described above can be modified or combined with any other individual features and concepts discussed herein to form alternate embodiments of the present invention.

We claim:

1. A method for ablating a target tissue within an organ of a body comprising:
   inserting a directional microwave ablation device into the body containing the target tissue to be ablated, the directional microwave ablation device being configured to provide a directional pattern for delivery of electromagnetic energy to the target tissue,
   positioning the device in direct contact with, but without penetrating, the organ; and
   activating the device thereby causing an antenna to emit electromagnetic energy that is sufficiently strong to cause tissue ablation,
   wherein the electromagnetic energy is directed toward the target tissue within the adjacent organ and away from the tissue surrounding the organ,
   wherein the directional microwave ablation device includes
      a cylindrical elongate body having a proximal end, a distal end, and a constant diameter that houses the antenna and one or more electrically conductive members configured to help generate the directional pattern and shield the tissue surrounding the organ from the electromagnetic energy,
      a device tip positioned at the distal end and configured to transmit the electromagnetic energy to the target tissue, and
      a reinforcement plug or a rigid spacer positioned at the distal end and configured to support the electrically conductive members and the device tip.

2. The method of claim 1, wherein the tissue surrounding the organ is healthy tissue, and wherein the tissue ablation substantially ablates the entire target tissue while mitigating thermal damage to the surrounding healthy tissue.

3. The method of claim 1, wherein the target tissue is a tumor that resides near or extends inwardly from an outer surface of the organ.

4. The method of claim 1, wherein the directional microwave ablation device is inserted percutaneously, bronchoscopically, laparoscopically, endoscopically, endo-luminally, endo-vascularly, or during open surgery into the body.

5. The method of claim 1, wherein the target tissue comprises a tumor, and wherein the method comprises inserting a plurality of the directional microwave ablation devices having device antennas into the body containing the tumor, the device antennas being positioned within the body substantially outside the margins of the tumor, the activating of the devices causing ablation of the tumor from the outside of the tumor in toward the center of the tumor.

6. A method of ablating a target tissue within a human or animal body comprising:
   percutaneously inserting into the body a plurality of directional devices for delivering electromagnetic energy to the target tissue, wherein each of the plurality of directional devices comprise:
      an elongate body comprising a proximal end, a distal end, and at least one lumen interconnecting the proximal and distal ends;
      an antenna located within the at least one lumen and configured to emit electromagnetic energy therefrom sufficiently strong to cause tissue ablation;
      one or more electrically conductive members configured to help generate a directional pattern of the electromagnetic energy and to shield a tissue adjacent to the target tissue from the electromagnetic energy emitted from the antenna,
      a trocar tip positioned at the distal end and configured to transmit the electromagnetic energy to the target tissue, and
      a reinforcement plug or a rigid spacer positioned at the distal end and configured to support the electrically conductive members and the trocar tip;
   positioning the antennas of the plurality of directional devices into or adjacent to the target tissue to be ablated; and
   activating the plurality of devices thereby causing the antennas to emit electromagnetic radiation along a predetermined angular expanse that is sufficiently strong to cause ablation of the target tissue.

7. The method of claim 6, wherein the tissue to be ablated comprises a tumor.

8. The method of claim 6, wherein the plurality of directional devices are positioned adjacent to the target tissue, but without penetrating the target tissue.

9. The method of claim 6, wherein the plurality of directional devices is activated simultaneously.

10. The method of claim 6, wherein the plurality of directional devices is activated with power being cycled between the devices.

11. The method of claim 6, wherein the magnitude of the electromagnetic radiation emitted by one of the plurality of directional devices is different from the magnitude of the electromagnetic radiation emitted by one other of the plurality of directional devices.

12. A method for ablating a target tissue within an organ of a body comprising:
    inserting a directional microwave ablation device into the body containing the target tissue to be ablated, the directional microwave ablation device being configured to provide a directional pattern for delivery of electromagnetic energy to the target tissue,
    positioning the device in direct contact with, but without penetrating, the organ; and
    activating the device thereby causing an antenna to emit electromagnetic energy that is sufficiently strong to cause tissue ablation,
    wherein the electromagnetic energy is directed toward the target tissue within the adjacent organ and away from the tissue surrounding the organ,
    wherein the directional microwave ablation device includes a cylindrical elongate body having a constant diameter that houses the antenna and a plurality of electrically conductive tubular members configured to help generate the directional pattern and shield the tissue surrounding the organ from the electromagnetic energy,
    wherein the electrically conductive tubular members are configured to circulate a cooling fluid through at least one of the electrically conductive members and into the cylindrical elongate body.

13. The method of claim 12, wherein the tissue surrounding the organ is healthy tissue, and wherein the tissue ablation substantially ablates the entire target tissue while mitigating thermal damage to the surrounding healthy tissue.

14. The method of claim 12, wherein the target tissue is a tumor that resides near or extends inwardly from an outer surface of the organ.

15. The method of claim 12, wherein the directional microwave ablation device is inserted percutaneously, bronchoscopically, laparoscopically, endoscopically, endo-luminally, endo-vascularly, or during open surgery into the body.

16. The method of claim 12, wherein the target tissue comprises a tumor, and wherein the method comprises inserting a plurality of the directional microwave ablation devices having device antennas into the body containing the tumor, the device antennas being positioned within the body substantially outside the margins of the tumor, the activating of the devices causing ablation of the tumor from the outside of the tumor in toward the center of the tumor.

* * * * *